US00RE44017E

(19) United States
(12) Reissued Patent
Yu et al.

(10) Patent Number: US RE44,017 E
(45) **Date of Reissued Patent: *Feb. 19, 2013**

(54) N-ACETYL ALDOSAMINES, N-ACETYLAMINO ACIDS AND RELATED N-ACETYL COMPOUNDS AND THEIR TOPICAL USE

(76) Inventors: Ruey J. Yu, Chalfont, PA (US); Eugene J. Van Scott, Abington, PA (US)

( * ) Notice: This patent is subject to a terminal disclaimer.

(21) Appl. No.: 13/046,047

(22) Filed: Mar. 11, 2011

Related U.S. Patent Documents

Reissue of:
(64) Patent No.: 6,159,485
Issued: Dec. 12, 2000
Appl. No.: 09/227,213
Filed: Jan. 8, 1999

U.S. Applications:
(63) Continuation of application No. 12/722,170, filed on Mar. 11, 2010, which is a continuation of application No. 12/536,209, filed on Aug. 5, 2009, now Pat. No. Re. 42,902, which is a continuation of application No. 11/590,898, filed on Nov. 1, 2006, now Pat. No. Re. 41,339.

(51) Int. Cl.
*A61K 7/00* (2006.01)
(52) U.S. Cl. ..... 424/401; 514/2; 514/554; 514/557; 514/574; 514/844; 514/847
(58) Field of Classification Search ..... 424/401; 514/2, 554, 557, 574, 844, 847
See application file for complete search history.

(56) References Cited

U.S. PATENT DOCUMENTS

| | | | | |
|---|---|---|---|---|
| 3,697,652 | A | 10/1972 | Rovati et al. | |
| 3,856,934 | A * | 12/1974 | Kligman | 424/62 |
| 3,932,622 | A * | 1/1976 | Friedman et al. | 514/558 |
| 4,803,067 | A * | 2/1989 | Brunetta et al. | 424/63 |
| 4,870,061 | A | 9/1989 | Speck et al. | |
| 5,112,613 | A * | 5/1992 | Honda et al. | 424/400 |
| 5,296,500 | A * | 3/1994 | Hillebrand | 514/562 |
| 5,378,455 | A | 1/1995 | Kealey et al. | 424/73 |
| 5,401,770 | A * | 3/1995 | Taguchi et al. | 514/494 |
| 5,470,567 | A * | 11/1995 | Nair et al. | 424/59 |
| 5,525,336 | A | 6/1996 | Green et al. | 424/94.5 |
| 5,650,166 | A | 7/1997 | Ribier et al. | |
| 5,728,371 | A * | 3/1998 | Pinzon et al. | 424/59 |
| 5,767,158 | A * | 6/1998 | Suetsugu et al. | 514/563 |
| 5,776,920 | A * | 7/1998 | Quarles | 514/162 |
| 5,993,787 | A * | 11/1999 | Sun et al. | 424/59 |
| RE41,339 | E * | 5/2010 | Yu et al. | 424/401 |

FOREIGN PATENT DOCUMENTS

| | | | |
|---|---|---|---|
| EP | 0281812 | A1 | 9/1988 |
| EP | 0415598 | A1 * | 3/1991 |
| EP | 852946 | A2 | 7/1998 |
| GB | 1503564 | A | 3/1978 |
| GB | 2180153 | A * | 3/1987 |
| JP | 59013708 | A | 1/1984 |
| WO | 87/02244 | A1 | 4/1987 |
| WO | WO-97/35573 | * | 10/1997 |
| WO | 98/52576 | A1 | 11/1998 |

OTHER PUBLICATIONS

Ortonne, "Pigmentary Changes of the Ageing Skin", 1990, British Journal of Dermatology, 122 Supp. 35, pp. 21-28.*
Yano H. et al., "Effects of N-Acetyl-D-Glucosamine on Wound Healing in Rats", Mie Medical Journal, TSU, JP, vol. XXXV, No. 1, 1985, pp. 53-56, XP002997084, ISSN: 0026-3532.
European Search Report in related application 10 00 6974 mailed Mar. 7, 2011.

* cited by examiner

*Primary Examiner* — Ali Soroush
(74) *Attorney, Agent, or Firm* — Pillsbury Winthrop Shaw Pittman LLP

(57) ABSTRACT

Compositions comprising N-acetyl-aldosamines, N-acetylamino acids, and related N-acetyl compounds are useful to alleviate or improve various cosmetic conditions and dermatological disorders, including changes or damage to skin, nail and hair associated with intrinsic aging and/or extrinsic aging, as well as changes or damage caused by extrinsic factors. N-acetyl-aldosamines, N-acetylamino acids, and related N-acetyl composition may further comprise a cosmetic, pharmaceutical or other topical agent to enhance or create synergetic effects.

23 Claims, No Drawings

N-ACETYL ALDOSAMINES, N-ACETYLAMINO ACIDS AND RELATED N-ACETYL COMPOUNDS AND THEIR TOPICAL USE

Matter enclosed in heavy brackets [ ] appears in the original patent but forms no part of this reissue specification; matter printed in italics indicates the additions made by reissue.

*Notice: This is a continuation reissue application of continuation reissue application Ser. No. 12/722,170 filed Mar. 11, 2010, which is a continuation reissue application of continuation reissue application Ser. No. 12/536,209 filed Aug. 5, 2009 now U.S. Pat. No. Re. 42,902, which is a continuation reissue application of reissue application Ser. No. 11/590,898 filed Nov. 1, 2006 now U.S. Pat. No. Re. 41,339, which is a reissue application of U.S. Pat. No. 6,159,485.*

FIELD OF THE INVENTION

This application relates to topical compositions containing N-acetyl-aldosamines, N-acetylamino acids, and related N-acetyl compounds, and their use in alleviating or improving various cosmetic conditions and dermatological disorders including signs of aging, changes or damage to skin, nail and hair associated with intrinsic aging and/or extrinsic aging, as well as changes or damage caused by extrinsic factors such as sunlight, radiation, air pollution, wind, cold, heat, dampness, chemicals, smoke, and cigarette smoking; and for certain skin disorders associated with or due to itching and/or inflammation.

BRIEF DESCRIPTION OF THE PRIOR ART

In our U.S. Pat. No. 5,091,171 we described and claimed preventive as well as therapeutic treatment to alleviate cosmetic conditions and symptoms of dermatologic disorders with amphoteric compositions containing alpha hydroxyacids, alpha ketoacids, polymeric forms of hydroxyacids, and related compounds or. In our U.S. Pat. No. 5,547,988, and related patents, we described the use of topical compositions comprising a 2-hydroxycarboxylic acid or related compound to alleviate or improve signs of skin, nail and hair changes associated with intrinsic or extrinsic aging. In our U.S. Pat. No. 5,385,938, and related patents, we described preventive and therapeutic treatment to alleviate cosmetic conditions and symptoms of dermatologic disorders with amphoteric compositions containing alpha hydroxy acids, alpha ketoacids, polymeric forms of hydroxy acids, and related compounds or. In our U.S. Pat. No. 5,258,391 entitled "Phenyl Alpha Acyloxyalkanoic Acids, Derivatives and Their Therapeutic Use" we described and claimed the use of topical compositions containing phenyl alpha acyloxyalkanoic acids and derivatives to enhance the keratization of nails, skin, lips and other mucous membranes. In our U.S. Pat. No. 5,665,776 entitled "Additives Enhancing Topical Actions of Therapeutic Agents" we described and claimed the use of hydroxycarboxylic acids or related compounds to increase the cosmetic or therapeutic effect of cosmetic or pharmaceutical agents. In our U.S. Pat. No. 5,641,475 we described and claimed the use of topical compositions containing a bioactive cosmetic, dermatologic or preservative agent and aryl 2-acetoxyethanoic acid effective as a synergist or amplifier. In our U.S. Pat. No. 5,643,949 also entitled "Phenyl Alpha Acyloxyalkanoic Acids, Derivatives and Their Therapeutic Use" we described and claimed the use of topical compositions containing a cosmetic or dermatologic drug for topical administration to nails, skin and lips and an amount of a phenyl alpha acyloxyalkanoic acid or derivatives effective to enhance the cosmetic or therapeutic effect of the dermatologic drug. In U.S. Pat. No. 4,603,146 to Albert M. Kligman, disclosure is made of the use of vitamin A (tretionoin) to reduced and prevent epithelial growths and aid the skin in regaining and maintaining firmness, turgor and elasticity.

In a report entitled "Topical Tretinoin for Photoaged Skin" by Kligman el al., J. American Academy of Dermatology, Vol. 15, pages 836-859, 886-887 (1986), daily topical application of 0.05% tretinoin (also known as all-transretinoic acid) in a cream has been found to improve photodamaged skin. In another report entitled "Topical Tretinoin Improves Photoaged Skin: A Double-blind Vehicle-controlled Study" by Weiss et al., J. American Medical Association, Vol. 259 pages 527-532 (1988), daily topical application of 0.1% tretinoin as compared to vehicle alone application for 16 weeks has been shown to improve photoaged skin. One side-effect has been a dermatitis encountered by 92% of the patients participating in this study. The dermatitis was characterized by a patchy erythema, localized swelling, dry skin, and mild scaling. Patients complained about burning, tingling, or pruritus. In yet another report entitled "Topical Tretinoin in the Treatment of Aging Skin" by Weiss et al., J. American Academy of Dermatology Vol. 19, pages 169-175 (1988), topical application of 0.1% tretinoin cream for 8 to 12 months has been found to improve clinical signs of aging skin. The side effects have been burning sensation in the eyes and mild skin irritations.

In PCT Application No. PCT/US96/16534, filed Oct. 16, 1996, entitled "Topical Compositions Containing N-Acetylcysteine and Odor Masking Materials," topical compositions comprising from 0.01% to 50% of N-acetylcysteine or a derivative of N-acetylcysteine, from 0.01% to 0.5% of an odor masking material, and a topical carrier are disclosed to improve the appearance of skin.

N-Acetylcysteine is N-acetylated cysteine which is a thiol containing amino acid, also called α-acetamido-β-mercaptopropanoic acid. Topical compositions containing N-acetylcysteine have been claimed to improve physical appearance of the skin including cosmetic wrinkles. N-acetylcysteine contains a free thiol group, thus, is known as an antioxidant. The affect of N-acetylcysteine is claimed to be due to its antioxidant property. N-Acetylcysteine, as an antioxidant substance, also has been indicated as protective against pulmonary oxygen toxicity (Eur. Respir. J. 2, 116-126, 1989).

N-acetylcysteine, however, is also associated with a number of significant drawbacks. N-acetylcysteine is known to degrade under ordinary storage conditions and result in a malodorous smell. The malodor is suggested to be caused by the release of thiol compounds and hydrogen sulfide upon degradation. Thus, topical compositions containing N-acetylcysteine have little or no commercial use due to the strong malodor of N-acetylcysteine.

PCT/US96/16534 claimed that the malodor could be masked by addition of certain perfume chemicals at concentrations ranging from 0.01 to 0.5% by weight. The perfume chemicals include aromatic esters, aliphatic esters, aromatic alcohol, aliphatic alcohols, aliphatic ketones, aromatic aldehydes, aliphatic aldehydes, aromatic ethers and aliphatic ethers. Because the malodorous thiol compounds and hydrogen sulfide have not been chemically neutralized or destroyed, however, the transient masking effect is not a satisfactory solution for most consumers, and therefore is not a viable approach for commercialization of N-acetylcysteine in cosmetic industry.

We have now discovered that N-aldosamines, N-acetylated amino acids and related compounds are topically effective for various cosmetic conditions and dermatological indications including the signs of skin, nail and hair changes associated with intrinsic and/or extrinsic aging. The N-acetylated amino acids and related compounds do not necessarily contain thiol groups and are not necessarily antioxidants.

SUMMARY OF THE INVENTION

Accordingly, it is an object of this invention to provide methods and compositions which can alleviate various cosmetic conditions and dermatological disorders including the signs of skin, nail and hair changes associated with intrinsic and/or extrinsic aging and extrinsic factors, and other skin conditions associated with or due to itching and/ or inflamation, including pruritus.

We have now discovered that N-acetyl aldosamines, N-acetylamino acids and related N-acetyl compounds have unexpected properties. Topical applications of compositions comprising N-acetyl aldosamines, N-acetylamino acids and related N-acetyl compounds have been found to improve cosmetic conditions and dermatological disorders including cosmetic as well as clinical signs of changes in skin, nails and hair associated with intrinsic and/or extrinsic aging, or the damages caused by extrinsic factors such as sunlight, radiation, air pollution, wind, cold, dampness, heat, chemicals, smoke, and cigarette smoking.

The signs of skin changes associated with intrinsic and/or extrinsic aging and the skin damages caused by extrinsic factors include thinning of skin; fragile skin; deepening of skin lines and fine lines; wrinkles, including fine and course wrinkles; blemishes; atrophy; pigmented spots, blotches and mottles, nodules and mottled skin; pre-cancerous lesions; elastotic changes characterized by leathery, lusterless, uneven, coarse, rough, dry and/or yellowish skin; loss of skin elasticity and recoilability; loss of skin lubricating substances; changes in qualities and quantities of glycosaminoglycans and proteoglycans and collagen and elastic fibers; solar elastosis; decrease in collagen fibers; diminution in the number and diameter of elasitic fibers in the papillary dermis; atrophy; stretch marks; reduction in subcutaneous adipose tissue; deposition of abnormal elastic materials in the dermis leading to thickening of the dermis; older-looking skin; and telangiectatic skin.

The signs of nails and hair changes associated with intrinsic aging and the damages caused by extrinsic factors include thinning, fragility, splitting, lack of luster, uneven surface, and loss of flexibility and elasticity.

In accordance with the objects of the invention, a composition comprising at least one compound selected from the group consisting of N-acetyl aldosamines, N-acetylamino acids and related compounds, present in a therapeutically effective amount and in a pharmaceutically acceptable vehicle for topical treatment of cosmetic conditions or dermatological disorders is provided. In one embodiment of the invention, the composition further comprises a cosmetic, pharmaceutical, or other topical agent.

Also in accordance with the objects of the invention, a method for treating cosmetic conditions and dermatological disorders comprising topically applying a therapeutically effective amount of a composition comprising at least one compound selected from the group consisting of N-acetyl aldosamines, N-acetylamino acids and related compounds, in a pharmaceutically acceptable vehicle is provided. In one embodiment of the invention, the method comprises topically applying a therapeutically effective amount of a composition comprising at least one compound selected from the group consisting of N-acetyl aldosamines, N-acetylamino acids and related compounds, and at least one cosmetic, pharmaceutical, or other topical agent, in a pharmaceutically acceptable vehicle.

N-Acetyl aldosamines, N-acetylamino acids and related N-acetyl compounds which are useful for topical treatment of skin, nail and hair changes associated with intrinsic and/or extrinsic aging and extrinsic factors include, inter alia, N-acetyl-aldosamines which are derivatives of aminosugars and include N-acetyl-ribosamine, N-acetyl-arabinosamine, N-acetyl-glucosamine, N-acetyl-galactosamine and N-acetyl-mannosamine, and N-acetylamino acids which are N-acetyl derivatives of amino acids and include N-acetyl-glycine, N-acetyl-proline, N-acetyl-lysine, N-acetyl-arginine and N-acetyl-tryptophan.

Additional objects and advantages of the invention will be set forth in part in the description that follows, and in part will be obvious from the description, or may be learned by practice of the invention. The objects and the advantages of this invention may be realized and obtained by means of the compositions and methods particularly pointed out in the appended claims.

DETAILED DESCRIPTION OF THE PREFERRED EMBODIMENTS

1. N-Acetyl-aldosamines, N-Acetylamino Acids and Related N-Acetyl Compounds

(i) N-Acetyl-aldosamines

One aspect of the present invention pertains to compositions comprising N-acetyl-aldosamines and related compounds. N-acetyl-aldosamines are N-acetylated aminosugars in which the acetylamino group is preferably located at position 2 of the carbon chain. In accordance with the present invention, the generic structure or formula of N-acetyl-aldosamines which are topically beneficial for various cosmetic and dermatologic indications may be represented as follows:

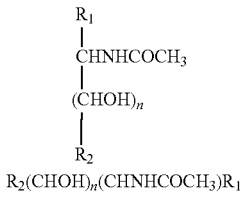

where n is an integer, preferably 1-19; $R_1$ is selected from the group consisting of CHO, $CONH_2$, and $COOR_3$; $R_2$ is selected from the group consisting of H, I, F, Cl, Br, and an alkyl, alkoxyl, aralkyl or aryl group of saturated or unsaturated, isomeric or non-isomeric, straight or branched chain or cyclic form, having 1 to 19 carbon atoms; and $R^3$ is selected from the group consisting of H, an alkyl, aralkyl or aryl group having 1 to 9 carbon atoms. N-Acetyl-aldosamines may be present as saturated or unsaturated, isomeric or non-isomeric, straight or branched chain or cyclic form. A typical cyclic form of an N-acetyl-aldosamine is a five member ring (furanose form) or a six member ring (pyranose form).

The following are some representative N-acetyl-aldosamines and related compounds: N-acetyl-glycerosamine, N-acetyl-erythrosamine, N-acetyl-threosamine, N-acetyl-ribosamine, N-acetyl-arabinosamine, N-acetyl-xylosamine, N-acetyl-lyxosamine, N-acetyl-allosamine, N-acetyl-altrosamine, N-acetyl-glucosamine, N-acetyl-mannosamine, N-acetyl-gulosamine, N-acetyl-idosamine, N-acetyl-galactosamine, N-acetyl-talosamine, N-acetyl-glucoheptosamine, N-acetyl-galactoheptosamine, N-acetyl-mannoheptosamine, N-acetyllactosamine, N-acetylmuramic acid, N-acetyl-neuramine, N-acetylneuramin Lactose, N-acetyl-glyceraminic acid, N-acetyl-erythrosaminic acid, N-acetyl-threosaminic acid, N-acetyl-ribosaminic acid, N-acetyl-arabinosaminic acid, N-acetyl-xylosaminic acid, N-acetyl-lyxosaminic acid, N-acetyl-allosaminic acid, N-acetyl-altrosaminic acid, N-acetyl-glucosaminic acid, N-acetyl-mannosaminic acid, N-acetyl-gulosaminic acid, N-acetyl-idosaminic acid, N-acetyl-galactosaminic acid, N-acetyl-talosaminic acid, N-acetyl-heptoglucosaminic acid, N-acetyl-heptogalactosaminic acid, N-acetyl-heptomannosaminic acid, and N-acetyl-N-acetylneuraminic. The amides and esters of the foregoing acid compounds also are contemplated by the present invention. Examples of five and six member ring forms are 2-acetamido-2-deoxy-D-ribofuranoside, 2-acetamido-2-deoxy-D-ribopyranoside, 2-acetamido-2-deoxy-D-glucofuranoside, 2-acetamido-2-deoxy-D-glucopyranoside, 2-acetamido-2-deoxy-D-galactofuranoside and 2-acetamido-2-deoxy-D-galactopyranoside.

(ii) N-Acetylamino Acids

Another aspect of the invention pertains to compositions comprising N-acetylamino acids and related compounds. N-acetylamino acids are N-acetyl derivatives of amino acids. In accordance with the present invention, the generic structure or formula of N-acetylamino acids and related compounds which are topically beneficial for various cosmetic and dermatologic indications may be represented as follows:

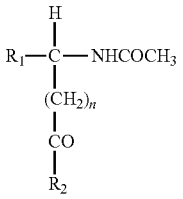

$R_1CH(NHCOCH_3)(CH_2)_nCOR_2$ where $R_1$ is H, or an alkyl or aralkyl group having 1 to 14 carbon atoms; n is an integer, preferably from 0 to 5; $R_2$ is OH, $NH_2$ or $OR_3$; and $R_3$ is an alkyl, aralkyl or aryl group having 1 to 9 carbon atoms; the alkyl, aralkyl or aryl group may be saturated or unsaturated, isomeric or non-isomeric, straight or branched chain or cyclic form; and in addition $R_1$ may carry OH, SH, $SCH_3$, COOH, $NH_2CONH_2$, guanidine or heterocyclic group; the H attached to a carbon atom may be substituted by I, F, Cl, Br or alkoxyl group having 1 to 9 carbons. N-Acetylamino acids may be present as isomeric or non-isomeric, as a free acid, salt, lactone, amide or ester form.

The following are some representative N-acetylamino acids and related compounds: N-acetyl-glycine, N-acetyl-alanine, N-acetyl-valine, N-acetyl-leucine, N-acetyl-isoleucine, N-acetyl-serine, N-acetyl-threonine, N-acetyl-tyrosine, N-acetyl-cysteine, N-acetyl-methionine, N-acetyl-aspartic acid, N-acetyl-asparagine, N-acetyl-glutamic acid, N-acetyl-glutamine, N-acetyl-arginine, N-acetyl-lysine, N-acetyl-histidine, N-acetyl-phenylalanine, N-acetyl-tyrosine, N-acetyl-tryptophan, N-acetyl-proline, N-acetyl-β-alanine, N-acetyl-taurine, N-acetyl-r-aminobutanoic acid, N-acetyl-hydroxyproline, N-acetyl-canavanine, N-acetyl-hydroxylysine, N-acetyl-cycloserine, N-acetyl-homoarginine, N-acetyl-norleucine, N-acetyl-norvaline, N-acetyl-homoserine, N-acetyl-methylserine, N-acetyl-hydroxyvaline, N-acetylethionine, N-acetyl-methoxinine, N-acetyl-β-aminoisobutanoic acid, N-acetyl-homocysteine, N-acetyl-cysteine sulfinic acid, N-acetyl-homophenylalanine, N-acetyl-homotryptophan, N-acetyl-5-hydroxytryptamine (N-acetylserotonin), N-acetyltryptamine, N-acetyl-ornithine, N-acetyl-citrulline, N-acetyl-argininosuccinic acid, N-acetyl-dopa, N-acetyl-3-iodotyrosine, N-acetyl-3,5-diiodotyrosine, N-acetyl-3,5,3'-triiodothyronine, N-acetyl-thyroxine, N-acetyl-creatine, N-acetyl-creatinine, N-acetyl-cystine and N-acetyl-homocystine.

The above N-acetylamino acids and related N-acetyl compounds may be present as a free acid, salt, lactone, amide or ester form. Examples of these compounds include N-acetyl-cysteine ammonium salt, N-acetyl-homocysteine thiolactone, N-acetyl-L-cystine methyl ester, N-acetyl-L-tryosinamide, N-acetyl-L-tryosine ethyl ester, N-acetyl-serine amide, N-acetylglycine methyl ester, N-acetylglycinamide, and N-acetyl-tryptophan methyl, ethyl, propyl or isopropyl esters.

The related N-acetyl compounds may also include dimers and oligomers formed from N-acetylamino acids with 2 to 5 monomer units. Examples include N-acetylglycylglycine and its amide and esters, N-acetylglycyl-leucine its amide and esters, N-acetylglycyltryptophan, N-acetylglycyl-glutamic acid and its amide and esters, N-acetyltryosyl-phenylalanine and its amide and esters, N-acetylglycyl-lysine and its amide and esters, N-acetylleucyl-glycine and its amide and esters, N-acetylglycyl-glycyl-glycine and its amide and esters, N-acetylglycyl-lysyl-hydroxyproline and its amide and esters.

A preferred group N-Acetylamino acids and related compounds are the group of compounds represented by the generic structure or formula above, but excluding N-acetyl-cysteine and derivatives of N-acetylcysteine. N-acetylcysteine is known to degrade under ordinary storage conditions and result in a malodorous smell. The malodor is suggested to be caused by the release of thiol compounds and hydrogen sulfide upon degradation. Because N-acetylcysteine and its derivatives are malodorous, they are less preferred for use in the present invention.

2. Topical Uses of N-Acetyl-aldosamines, N-Acetylamino Acids and Related N-Acetyl Compounds (i) N-Acetyl-aldosamines, N-Acetylamino Acids and Related N-Acetyl Compounds Compositions comprising the N-acetyl-aldosamine, N-acetylamino acid or related N-acetyl compounds described herein are topically beneficial for various cosmetic conditions and dermatologic disorders, including those associated with intrinsic and/or extrinsic aging, as well as with changes or damage caused by extrinsic factors. These compositions can comprise one or more than one N-acetyl-aldosamine, N-acetylamino acid or related N-acetyl compound. In a preferred embodiment, the compositions may be used for skin, hair and nail changes associated with intrinsic and/or extrinsic aging, and changes or damage caused by extrinsic factors.

With respect to age associated skin changes, the underlying bases of these changes is described in U.S. Pat. No. 4,603,146 (Kligman). In particular, the underlying causes of skin changes associated with aging can be more easily understood in view of the following summary of the changes in the epidermis and dermis as aging progresses.

With increasing age and exposure of a human to sun and other environmental traumas, cells divide at a slower rate (decreased capacity to renew themselves). They show marked irregularities in size, shape and staining properties; orderliness (polarity) from below to above is lost. The thickness of the epidermis decreases (atrophy). The horny layer which comprises the barrier against water loss and penetration of chemicals becomes abnormal due to the shedding (exfoliation) of cells in large group or clusters instead of as individual cells, resulting in roughness, scaling and dryness. There is loss of the orderly transformation of living epithelial cells into cornified dead cells which are shed at the surface, that is, differentiation is impaired. Aberrant differentiation results in numerous foci of abnormal epithelial growths or tumors, the most frequent and important of which are actinic keratoses. After many years these can transform into frank skin cancers called basal cell and squamous cell cancers. Pigment producing cells (melanocytes) can also become altered forming flat, dark growths (lentigo melanoma) which may progress to malignant melanoms.

The cells which make the fibers of the dermis become smaller and sparser with increasing age, usually in sun-damaged facial skin. There is a great loss of collagen fibers resulting in looseness and easy stretchability of the skin; elastic fibers become abnormal so that the skin does not promptly snap back after being stretched. Since the fibrous components comprise more than 90% of the bulk of skin of which 95% is collagen, the degradation of these fibers, especially collagen, is mainly responsible for wrinkling, laxness and loss of elasticity.

Additionally, small blood vessels become thin walled, dilated and often ruptured. Vascular supply thereby becomes compromised.

The signs of nail and hair changes associated with intrinsic aging and the damages caused by extrinsic factors include thinning of hair and nail plate; lack of lubricants and luster, and uneven surface of hair and nails; fragility and splitting of hair and nails; and reduction of flexibility, resiliency, and elasticity of hair and nails.

The conventional management of signs of aging skin has been the use of cosmetics, as well as medical procedures such as phenol, trichloroacetic acid, and other chemical peels, and plastic surgery, etc. Such medical procedures are costly and risky with serious side effects, and the treatments alter only the cosmetic appearance of the skin, without any significant modifications of the underlying aging process.

Topical application to the skin, hair or nails of a composition of the present invention is beneficial for various cosmetic conditions and dermatologic disorders including those associated with intrinsic and/or extrinsic aging and extrinsic factors, and also including those characterized by the foregoing changes to the skin, hair and nails. Exemplary indications are characterized as disturbed keratinization, defective syntheses of dermal components, and changes associated with aging of skin, nail and hair; and those indications which include dryness or loose or skin, nail and hair; xerosis; ichthyosis; palmar and plantar hyperkeratoses; uneven and rough surface of skin, nail and hair; dandruff; Darier's disease; lichen simplex chronicus; keratoses; acne; pseudofolliculitis barbae; eczema; psoriasis; itchy scalp and skin; pruritus; warts; herpes; age spots; lentigines; melasmas; blemished skin; hyperkeratoses; hyperpigmented skin; abnormal or diminished syntheses of collagen, glycosaminoglycans, proteoglycans and elastin as well as diminished levels of such components in the dermis; stretch marks; skin lines; fine lines; wrinkles; thinning of skin, nail plate and hair; skin thickening due to elastosis of photoaging, loss or reduction of skin, nail and hair resiliency, elasticity and recoilability; lack of skin, nail and hair lubricants and luster; dull and older-looking skin, nail and hair; fragility and splitting of nail and hair; and other topical conditions and indications.

(ii) Combination Compositions

In addition, compositions comprising one or more than one N-Acetyl-aldosamine, N-acetylamino acid and related N-acetyl compound may also be incorporated into a composition comprising a cosmetic, pharmaceutical or other topical agent to enhance or create synergetic effects.

In accordance with this aspect of the invention, the compositions of the present invention may contain one or more N-Acetyl-aldosamine, N-acetylamino acid and related N-acetyl compounds to magnify the therapeutic effect of an unrelated cosmetic or pharmaceutical agent. At least one compound selected from the group consisting of N-Acetyl-aldosamine, N-acetylamino acid and related N-acetyl compounds may be incorporated into composition containing a cosmetic or pharmaceutical agent for topical treatment to improve or alleviate signs of skin, nails or hair changes associated with intrinsic aging or the damages caused by extrinsic factors. It has been found that such incorporation results in magnified therapeutic efficacies which are not simply additive effects.

Most pharmaceutical drugs produce their therapeutic effects by first interacting with their receptors in the target tissues. Many drug receptors are functional macromolecules such as enzymes, cell membrane components or certain components of cells. The binding affinity or interacting property of a drug toward its specific receptor molecule is intimately governed by the chemical structure of the drug. Since most pharmaceutical agents are chemically different from N-acetyl compounds of the instant invention, the respective receptor molecule should be different and so are the pharmacological actions and the therapeutic effects. Under such conditions if N-Acetyl-aldosamine, N-acetylamino acid and/or a related N-acetyl compound is incorporated into a composition containing a pharmaceutical agent, one of the following two consequences may arise:

(a) No enhancement or any substantial changes in either effect. In this case, the overall clinical effect would be a mixed effect, i.e. the effect due to the pharmaceutical agent alone mixed with the effect due to N-Acetyl-aldosamine, N-acetylamino acid or related N-acetyl compound alone. Also in this case, the interaction between the pharmaceutical agent and its receptor molecule is not affected nor interfered by the presence of N-Acetyl-aldosamine, N-acetylamino acid or related N-acetyl compound. Nor does the N-Acetyl-aldosamine, N-acetylamino acid or related N-acetyl compound assist in or enhance the binding affinity or the interaction of the pharmaceutical agent toward its receptor molecule. The clinical results from such combination composition would be just the mixed effects.

(b) Amplified therapeutic action or substantial loss of therapeutic action in either effect. In this case, the interaction between the pharmaceutical agent and its receptor molecule is affected either positively or negatively by the presence of a N-Acetyl-aldosamine, N-acetylamino acid or related N-acetyl compound. From the point of positive effect, N-Acetyl-aldosamine, N-acetylamino acid or the related N-acetyl compound may produce an amplified effect by either increasing the affinity of the receptor molecule toward the pharmaceutical agent; acting as a better and more efficient coenzyme or as an activator by disrupting barriers and removing obstacles for better binding of the agent toward its receptor molecule; for example, enzyme activation by removal of natural inhibitors. In all these cases the overall clinical results would be due to magnified therapeutic effects which are not predictable from either effect alone.

From the point of negative effect, a N-Acetyl-aldosamine, N-acetylamino acid or related N-acetyl compound might interfere with or decrease the binding affinity of the pharmaceutical agent toward its receptor molecule; i.e. acting as an competitor or inhibitor. In such case, the overall clinical results should be due to substantial diminishment or completely loss of therapeutic effects, which is also unpredictable from either effect alone.

We have found that, in most cases, therapeutic effects of cosmetic and pharmaceutical agents are amplified when a N-acetyl-aldosamine, N-acetylamino acid or related N-acetyl compound is incorporated into the composition, i.e., consequence (b) above is observed.

The cosmetic and pharmaceutical agents which may be actuated by N-Acetyl-aldosamine, N-acetylamino acid or a related N-acetyl compound include those that improve or eradicate age spots, keratoses and wrinkles; local analgesics and anesthetics; antiacne agents; antibacterials; antiyeast agents; antifungal agents; antiviral agents; antidandruff agents; antidermatitis agents; antihistamine agents; antipruritic agents; antiemetics; antimotion sickness agents; antiinflammatory agents; antihyperkeratolytic agents; antiperspirants; antipsoriatic agents; antiseborrheic agents; hair conditioners and hair treatment agents; antiaging and antiwrinkle agents; sunblock and sunscreen agents; skin lightening agents; depigmenting agents; vitamins; corticosteroids; tanning agents; hormones; retinoids; and other dermatologicals.

Some examples of cosmetic and pharmaceutical agents are clotrimazole, ketoconazole, miconazole, griseoflivin, econazole, metronidazole, hydroxyzine, diphenhydramine, pramoxine, lidocaine, procaine, mepivacaine, monobenzone, erythromycin, tetracycline, clindamycin, meclocycline, hydroquinone, hydroquinone monoether, minocycline, naproxen, ibuprofen, theophylline, cromolyn, albuterol, retinol, retinyl acetate, retinyl palmitate, retinal, retinoic acid, 13-cis retinoic acid, hydrocortisone, hydrocortisone 21-acetate, hydrocortisone 17-valerate, hydrocortisone 17-butyrate, betamethasone valerate, betamethasone dipropionate, triamcinolone acetonide, fluocinonide, clobetasol, propionate, benzoyl peroxide, kojic acid, crotamiton, propranolol, promethazine, salicylic acid, vitamin E and vitamin E acetate.

Another example of cosmetic or other agents that may be combined with one or more N-acteyl-aldosamines, N-acetylamino acids or related N-acetyl compounds include hydroxyacids, ketoacids and related compounds. Examples of hydroxy acids include hydroxymonocarboxylic acids, hydroxydicarboxylic acids, 2-hydroxycarboxylic acids, other hydroxycarboxylic, 2-ketocarboxylic acids acids and related compounds. See, for example, U.S. Pat. Nos. 5,422,370, 5,547,988, 5,470,880, and 5,385,938. The hydroxy acids may exist as a free acid, an ester, a lactone, in salt form with an organic base or an inorganic alkali, and as stereoisomers. Representative examples of hydroxy acids and related compounds include glycolic acid, mandelic acid, lactic acid, tropic acid, methyllactic acid, lactobionic acid, tartaric acid, citric acid, glucuronic acid, ribonic acid, gluconolactone, ribonolactone, gycolyl glycollate, lactyl lactate, trilactic acid and polylactic acid.

Yet another example of cosmetic or other agents that may be combined with one or more N-acteyl-aldosamines, N-acetylamino acids or related N-acetyl compounds include phenyl alpha acyloxyalkanoic acids and derivatives thereof. These compounds may exist in a free acid, lactone or salt form, or as stereoisomers. See, for example, U.S. Pat. Nos. 5,258,391 and 5,643,949. Representative example of such compounds include diphenyl alpha acetoxyacetic acid, phenyl alpha acetoxyacetic acid, phenyl alpha methyl alpha acetoxyacetic acid, phenyl alpha acetoxypropanoic acid, and 2-phenyl beta acetoxypropanoic acid.

3. General Preparation of the Cosmetic and Therapeutic Compositions

Compositions comprising N-acetyl-aldosamine, N-acetylamino acid or related N-acetyl compounds of the instant invention may be formulated as solution, gel, lotion, cream, ointment, shampoo, spray, stick, powder, masque or other form topically acceptable for use on skin, nail and hair.

To prepare a solution composition, at least one N-acetyl compound of the instant invention is dissolved in a solution prepared from water, ethanol, propylene glycol, butylene glycol, diisopropyl adipate and/or other topically acceptable vehicle. The concentration of a single N-acetyl compound or the total concentration of all N-acetyl compounds, where the composition comprises more than one N-acetyl compound, may range from 0.01 to 99.9% by weight of the total composition, with preferred concentration of from 0.1 to 50% by weight of the total composition and with more preferred concentration of from 0.5 to 25% by weight of the total composition. Contemplated embodiments of the instant invention include ranges of 0.1% to 0.2%, 0.2% to 0.3%, 0.3% to 0.4%, 0.4% to 0.5%, 0.5% to 0.6%, 0.6% to 0.7%, 0.7% to 0.8%, 0.8% to 0.9%, 0.9% to 1%, 1% to 2%, 2% to 3%, 3% to 4%, 4% to 5%, 5% to 6%, 6% to 7%, 7% to 8%, 8% to 9%, 9% to 10%, 10% to 14%, 14% to 18%, 18% to 22%, 22% to 26%, 26% to 30%, 30% to 35%, 35% to 40%, 40% to 45%, 45% to 50%, 50% to 60%, 60% to 70%, 70% to 80%, 80% n to 90%, and 90% to 99.9% by weight of the total composition.

To prepare a topical composition in lotion, cream or ointment form, the N-acetyl compound is first dissolved in water, ethanol, propylene glycol, diisopropyl adipate and/or another vehicle, and the solution thus obtained is mixed with a desired base or pharmaceutically acceptable vehicle to make lotion, cream or ointment. Concentrations of the N-acetyl compound are the same as described above for the solution form.

A topical composition of the instant invention may also be formulated in a gel or shampoo form. A typical gel composition is formulated by the addition of a gelling agent such as chitosan, methyl cellulose, ethyl cellulose, polyvinyl alcohol, polyquaterniums, hydroxyethylcellulose, hydroxypropylcellulose, hydroxypropylmethylcellulose, carbomer or ammoniated glycyrrhizinate to a solution comprising the N-acetyl compound. The preferred concentration of the gelling agent may range from 0.1 to 4 percent by weight of the total composition. In the preparation of shampoo, the N-acetyl compound is first dissolved in water or propylene glycol, and the solution thus obtained is mixed with a shampoo base. Concentrations of the N-acetyl compound used in gel or shampoo form are the same as described above.

To prepare a combination composition for synergetic effects, a cosmetic, pharmaceutical or other topical agent is incorporated into any one of the above compositions by dissolving or mixing the agent into the formulation.

Other forms of compositions for topical delivery of N-acetyl compound of the instant invention are readily prepared or formulated by those skilled in the art.

The following are illustrative examples of formulations according to this invention. Although the examples utilize only selected compounds and formulations, it should be understood that the following examples are illustrative and not limiting. Therefore, any of the aforementioned N-acetyl compounds may be substituted according to the teachings of this invention in the following examples.

EXAMPLE 1

A typical N-acetyl-aldosamine, N-acetylamino acid or the related acetyl compound in a cream composition may be formulated as follows. N-Acetyl-α-D-glucosamine 10 g was dissolved in 30 ml warm water, and the solution thus obtained was mixed uniformly with 60 g cream base or commercially available hydrophilic ointment. The white cream thus formulated contained 10% N-acetyl-glucosamine. N-Acetyl-glucosamine 1% or 5% cream was formulated in the same manner except that N-acetyl-α-D-glucosamine 1 g or 5 g was used, and was dissolved in 39 ml or 35 ml water.

EXAMPLE 2

N-Acetyl-D-mannosamine 1 g was dissolved in 20 ml warm water, and the solution thus obtained was mixed uniformly with 79 g cream base or commercially available hydrophilic ointment. The white cream thus formulated contained 1% N-acetyl-mannosamine.

EXAMPLE 3

N-Acetyl-L-glutamine 0.5 g was dissolved in 20 ml water, and the solution thus obtained was mixed uniformly with 79.5 g cream base or commercially available hydrophilic ointment. The white cream thus formulated contained 0.5% N-acetyl-L-glutamine.

EXAMPLE 4

N-Acetyl-DL-proline 2 g was dissolved in 20 ml warm water, and the solution thus obtained was mixed uniformly with 78 g cream base or commercially available hydrophilic ointment. The white cream thus formulated contained 2% N-acetyl-proline.

EXAMPLE 5

N-Acetyl-glycine 3 g was dissolved in 20 ml water, and the solution thus obtained was mixed uniformly with 77 g cream base or commercially available hydrophilic ointment. The white cream thus formulated contained 3% N-acetyl-glycine.

EXAMPLE 6

N-Acetyl-L-arginine 4 g was dissolved in 20 ml water, and the solution thus obtained was mixed uniformly with 76 g cream base or commercially available hydrophilic ointment. The white cream thus formulated contained 4% N-acetyl-arginine.

EXAMPLE 7

A typical N-acetyl-aldosamine, N-acetylamino acid or related N-acetyl compound in a solution composition may be formulated as follows. N-acetyl-α-D-glucosamine 0.5 g was dissolved in 99.5 ml solution prepared from water 40 ml, ethanol 40 ml and propylene glycol 20 ml. The composition thus prepared contained 0.5% N-acetyl-glucosamine. N-Acetyl-glucosamine 5% in solution form was formulated in the same manner except that 5 g instead of 0.5 g active ingredient was dissolved in 95 ml solution.

EXAMPLE 8

N-Acetyl-D-galactosamine 1 g was dissolved in 99 ml solution prepared from water 40 ml, ethanol 40 ml and propylene glycol 20 ml. The composition thus prepared contained 1% N-acetyl-galactosamine.

EXAMPLE 9

N-Acetyl-L-tyrosinamide 2 g was dissolved in 98 ml solution prepared from water 40 ml, ethanol 40 ml and propylene glycol 20 ml. The composition thus prepared contained 2% N-acetyl-tyrosinamide.

EXAMPLE 10

N-Acetyl-L-lysine 0.5 g was dissolved in 99.5 ml solution prepared from water 40 ml, ethanol 40 ml and propylene glycol 20 ml. The composition thus prepared contained 0.5% N-acetyl-lysine.

EXAMPLE 11

N-Acetyl-L-tyrosine 0.2 g was dissolved in 99.8 ml solution prepared from water 40 ml, ethanol 40 ml and propylene glycol 20 ml. The composition thus prepared contained 0.2% N-acetyl-tyrosine.

EXAMPLE 12

N-Acetyl-L-cysteine methyl ester 0.5 g was dissolved in 99.5 ml solution prepared from water 40 ml, ethanol 40 ml and propylene glycol 20 ml. The composition thus prepared contained 0.5% N-acetyl-cysteine methyl ester.

EXAMPLE 13

N-Acetyl-L-tyrosine ethyl ester 3 g was dissolved in 97 ml solution prepared from ethanol 80 ml and propylene glycol 20 ml. The composition thus prepared contained 3% N-acetyl-tyrosine ethyl ester.

EXAMPLE 14

N-acetyl-L-cysteine 2 g was dissolved in 98 ml solution prepared from water 80 ml and propylene glycol 20 ml. The composition thus prepared contained 2% N-acetyl-cysteine.

EXAMPLE 15

A typical combination composition comprising for example N-acetyamino acid ester and hydrocortisone 17-valerate for eczema and other inflammatory dermatoses may be formulated as follows.

N-Acetyl-L-tyrosine ethyl ester 3 g and hydrocortisone 17-valerate 0.4 g were dissolved in 20 ml warm propylene glycol, and the solution thus obtained was mixed uniformly with 76.6 g cream base or commercially available hydrophilic ointment. The white cream thus formulated had pH 5.1, and contained 3% N-acetyl-L-tyrosine ethyl ester and 0.4% hydrocortisone 17-valerate.

EXAMPLE 16

A typical combination composition comprising for example N-acetylaldosamine and an anti-itch agent may be formulated as follows.

N-Acetyl-α-D-glucosamine 2 g was dissolved in 10 ml water and the solution was mixed with diphenhydramine 2 g in 4 ml water containing 2 g gluconolactone. The above solution was mixed uniformly with 80 g cream base or commercially available hydrophilic ointment. The composition with pH 5.1 contained 2% N-acetyl-D-glucosamine and 2% diphenhydramine.

A male subject, age 66, having an itchy lesion of lichen simplex chronicus on his right lower leg topically applied the above cream to the lesion. A few minutes after the topical application, the itch disappeared completely and the skin remained free of itch for the following 12 hours.

4. Application and Treatment Using N-Acetyl-Aldosamines, N-Acetylamino Acids and Related N-Acetyl Compounds The N-acetyl aldosamines, N-acetylamino acids and related N-acetyl compositions of the present invention may be applied to any area of the skin, hair, or nails. Exemplary areas of application include the hands, arms, neck, legs, feet, trunk, hair shaft, nails, including the nail plate and nail cuticle, and on and around the face. Exemplary areas of facial application include the nose, forehead, and areas around the eyes. The compositions may be applied with or without occlusion. Any suitable occlusive device may be used. In addition, it is within the knowledge of the skilled artisan how best to apply such occlusive devices to achieve the desired result.

The compositions of the present invention may be applied to these areas with varying frequency and for varying duration. In this regard, the skilled artisan will appreciate how to alter the frequency and duration of application to achieve the desired effect. For example, the compositions of the instant invention can be applied at varying frequencies including on a daily basis, 1 or more times daily, or 1 or more times weekly. When being applied on a daily basis, the instant invention can be applied 1, 2, 3 or more times a day. When being applied on a weekly basis the instant invention can be applied 1, 2, 3, 4, 5, 6, 7, 8, 9, 10, 11, 12 or more times a week. The duration of treatment with the compositions of the instant invention can also vary. For example, the compositions may be applied for 1, 2, 3, 4, 5, 6 or more weeks; or for 1, 2, 3, 4, 5, 6 or more months. The duration of treatment may also be continuous. Again, the skilled artisan will appreciate the interaction between frequency and duration of use in order to achieve and/or maintain the desired effect.

In addition, the skilled artisan will appreciate how to vary concentrations of the instant invention in conjunction with the frequency and duration of use to achieve the desired effect. For example, a composition of higher concentration might be applied with less frequency or for a shorter duration. In contrast, a composition of a lower concentration might be applied more frequently or for a longer duration.

TEST RESULTS

A Method of Measurement

In one of the studies related to skin changes associated with aging, skin thickness was measured by micrometer calipers as follows: The skin was grasped with a 2×6 cm metal hinge, the internal faces of the hinge were coated with emery cloth to prevent slippage, and manually squeezed to threshold subject discomfort. Combined thickness of two whole-skin layers including thickness of the two hinge leaves was measured with micrometer calipers. Thickness of the two hinge leaves was subtracted to determine the actual thickness of two whole-skin layers. Triplicate measurements on treated site were done and an average number was used for calculation of the skin thickness.

1. Xerosis and Dry Skin

A male subject, age 66, who had xerosis and dry skin on lower legs topically applied twice daily 5% N-acetyl-glucosamine cream for one week. After a few days of topical treatment, the skin became less rough and scaly, and felt smooth. The dry skin returned to normal-looking skin after one week of topical application. This result indicated that N-acetyl-glucosamine was therapeutically effective for topical treatment of xerosis and dry skin.

2. Acne

A female subject, age 27, who had adolescent acne with multiple papules and pustules on her face applied topically twice daily 5% N-acetyl-glucosamine solution. After a few days of treatment, most lesions became less inflamed and gradually eradicated. This result indicated that N-acetyl-glucosamine was therapeutically effective for topical treatment of acne.

3. Effect of an N-acetyl Compound on Skin

In order to determine biological effects of a topically applied N-acetyl compound of the instant invention, seven women and one man of ages ranging from 58 to 81 years participated in this study. Topical formulation for the study was N-acetyl-L-cysteine 2% in a solution prepared from water 80 ml and propylene glycol 20 ml.

Test sites were 1 cm square sites on extensor surface of forearm, 5 cm from the antecubital crease, a grid pattern formed by Hayes Test Chambers on Hayes adhesive strips. Each test chamber, 1 cm square, contained a square piece of filter paper which was fully moistened with 0.033 ml test solution.

Test chambers were impressed on the skin to leave outlines which were marked with Sanford Sharpie permanent marker. Sites were re-marked at each successive application of test solutions. Vehicle control sites were on the opposite forearm. Filter paper of each chamber was saturated with 0.033 ml solution and chambers were fixed in place with the Hayes adhesive tape that held the test and vehicle chambers. Chambers were removed twice weekly, and replaced with a new adhesive strip of chambers with filter paper moistened with test or vehicle solutions. The test was carried out for five weeks. Punch biopsy specimens, 3 mm or 4 mm in diameter, were secured at the end of the study, and specimens were processed and analyzed. Measurements of several tissue characteristics were also made.

Punch biopsy specimens obtained from test and control sites were placed immediately into the fixative, and processed for histochemical staining.

Epidermal thickness was measured with Micro Image Analysis System, and the mean thickness was expressed as area of epidermis/horizontal length. The thickness of papillary dermis (upper dermis) was also measured.

All the skin sites treated with N-acetyl-cysteine showed an average of 96% increase in thickness of epidermis over the control. In addition, all the test sites showed 47-227% increase in production of hyaluronic acid in papillary dermis over the control.

The above results indicated that N-acetyl compounds of the instant invention would be topically beneficial for treatment of various cosmetic or dermatologic indications including wrinkles and changes of skin, nail and hair associated with intrinsic and extrinsic aging.

4. Effect of N-acetyl-glucosamine on Skin

A female subject, age 74, applied topically twice daily 10% N-acetyl-glucosamine cream to her right forearm for three weeks. After three weeks her untreated left forearm was still loose, relatively thin and wrinkled when lifted. In contrast, her right forearm was more firm, smooth, plump and minimally wrinkled when lifted. While there was no change in skin thickness of her left forearm, her right forearm had increased 37% in skin thickness as measured by the micrometer calipers. This result indicated that N-acetyl-glucosamine would be therapeutically effective for topical treatment of wrinkles and changes of skin, nail or hair associated with aging.

5. Effect of N-acetyl-DL-homocysteine thiolactone on Skin

A male subject, age 76, applied topically twice daily 5% N-acetyl-DL-homocysteine thiolactone cream to his right forearm for three weeks. After three weeks his untreated left forearm was still loose, relatively thin and wrinkled when lifted. In contrast, his right forearm was more firm, smooth, plump and minimally wrinkled when lifted. While there was no change in skin thickness of his left forearm, his right forearm had increased 89% in skin thickness as measured by the micrometer calipers. This result indicated that N-acetyl-homocysteine thiolactone would be therapeutically effective for topical treatment of wrinkles and changes of skin, nail or hair associated with aging.

6. Effect of N-acetyl-L-cysteine on Skin

A female subject, age 71, applied topically twice daily 5% N-acetyl-L-cysteine cream to her right forearm for three weeks. After three weeks her untreated left forearm was still loose, relatively thin and wrinkled when lifted. In contrast, her right forearm was more firm, smooth, plump and minimally wrinkled when lifted. While there was no change in skin thickness of her left forearm, her right forearm had increased 14% in skin thickness as measured by the micrometer calipers. This result indicated that N-acetyl-cysteine would be therapeutically effective for topical treatment of wrinkles and changes of skin, nails or hair associated with aging.

7. Effect of N-acetyl-L-cysteine methyl ester on Skin

A female subject, age 59, applied topically twice daily 5% N-acetyl-L-cysteine methyl ester cream to her right forearm for three weeks. After three weeks her untreated left forearm was still loose, relatively thin and wrinkled when lifted. In contrast, her right forearm was more firm, smooth, plump and minimally wrinkled when lifted. While there was no change in skin thickness of her left forearm, her right forearm had increased 13% in skin thickness as measured by the micrometer calipers. This result indicated that N-acetyl-cysteine methyl ester would be therapeutically effective for topical treatment of wrinkles and changes of skin, nails or hair associated with aging.

8. Effect of N-acetyl-L-cysteine methyl ester on Skin

A female subject, age 72, applied topically twice daily 10% N-acetyl-L-cysteine methyl ester cream to her left forearm for three weeks. After three weeks her untreated right forearm was still loose, relatively thin and wrinkled when lifted. In contrast, her left forearm was more firm, smooth, plump and minimally wrinkled when lifted. While there was no change in skin thickness of her right forearm, her left forearm had increased 26% in skin thickness as measured by the micrometer calipers. This result indicated that N-acetyl-L-cystine methylester would be therapeutically effective for topical treatment of wrinkles and changes of skin, nail or hair associated with aging.

9. Effect of N-acetyl-L-cysteine methyl ester on Skin

A male subject, age 76, applied topically twice daily 5% N-acetyl-L-cysteine methyl ester cream to his left forearm for three weeks. After three weeks his untreated right forearm was still loose, relatively thin and wrinkled when lifted. In contrast, his left forearm was more firm, smooth, plump and minimally wrinkled when lifted. While there was no change in skin thickness of his right forearm, his left forearm had increased 87% in skin thickness as measured by the micrometer calipers. This result indicated that N-acetyl-cysteine methyl ester would be therapeutically effective for topical treatment of wrinkles and changes of skin, nail or hair associated with aging.

10. Effect of N-acetyl-DL-homocysteine thiolactone on Skin

A female subject, age 59, applied topically twice daily 5% N-acetyl-DL-homocysteine thiolactone cream to her left forearm for three weeks. After three weeks her untreated right forearm was still loose, relatively thin and wrinkled when lifted. In contrast, her left forearm was more firm, smooth, plump and minimally wrinkled when lifted. While there was no change in skin thickness of her right forearm, her left forearm had increased 21% in skin thickness as measured by the micrometer calipers. This result indicated that N-acetyl-homocysteine thiolactone would be therapeutically effective for topical treatment of wrinkles and changes of skin, nail or hair associated with aging.

11. Effect of N-acetyl-DL-tryptophan on Skin

A female subject, age 71, applied topically twice daily 10% N-acetyl-DL-tryptophan cream to her left forearm for three weeks. After three weeks her untreated right forearm was still loose, relatively thin and wrinkled when lifted. In contrast, her left forearm was more firm, smooth, plump and minimally wrinkled when lifted. While there was no change in skin thickness of her right forearm, her left forearm had increased 11% in skin thickness as measured by the micrometer calipers. This result indicated that N-acetyl-tryptophan would be therapeutically effective for topical treatment of wrinkles and changes of skin, nail or hair associated with aging.

12. Effect of N-acetyl-L-tyrosine ethyl ester on Skin

A female subject, age 47, applied topically twice daily 10% N-acetyl-L-tyrosine ethyl ester cream to her left forearm for four weeks. After four weeks her untreated right forearm was still loose, relatively thin and wrinkled when lifted. In contrast, her left forearm was more firm, smooth, plump and minimally wrinkled when lifted. While there was no change in skin thickness of her right forearm, her left forearm had increased 11% in skin thickness as measured by the micrometer calipers. This result indicated that N-acetyl-L-tyrosine ethyl ester would be therapeutically effective for topical treatment of wrinkles and changes of skin, nail or hair associated with aging.

13. Effect of N-acetyl-DL-tryptophan on Skin

A female subject, age 56, applied topically twice daily 10% N-acetyl-DL-tryptophan cream to her right forearm for three weeks. After three weeks her untreated left forearm was still loose, relatively thin and wrinkled when lifted. In contrast, her right forearm was more firm, smooth, plump and minimally wrinkled when lifted. While there was no change in skin thickness of her left forearm, her right forearm had increased 21% in skin thickness as measured by the micrometer calipers. This result indicated that N-acetyl-tryptophan would be therapeutically effective for topical treatment of wrinkles and changes of skin, nail or hair associated with aging.

14. Effect of N-acetyl-L-arginine on Skin

A female subject, age 47, applied topically twice daily 10% N-acetyl-L-arginine cream to her right forearm for four weeks. After four weeks her untreated left forearm was still loose, relatively thin and wrinkled when lifted. In contrast, her right forearm was more firm, smooth, plump and minimally wrinkled when lifted. While there was no change in skin thickness of her left forearm, her right forearm had increased 32% in skin thickness as measured by the micrometer calipers. This result indicated that N-acetyl-L-arginine would be therapeutically effective for topical treatment of wrinkles and changes of skin, nail or hair associated with aging.

15. Effect of N-acetyl-DL-tryptophan on Skin

A female subject, age 66, applied topically twice daily 10% N-acetyl-DL-tryptophan cream to her left forearm for five weeks. After five weeks her untreated right forearm was still loose, relatively thin and wrinkled when lifted. In contrast, her left forearm was more firm, smooth, plump and minimally wrinkled when lifted. While there was no change in skin thickness of her right forearm, her left forearm had increased 12% in skin thickness as measured by the micrometer calipers. This result indicated that N-acetyl-tryptophan would be therapeutically effective for topical treatment of wrinkles and changes of skin, nail or hair associated with aging.

16. Effect of N-acetyl-L-tyrosine ethyl ester on Skin

A female subject, age 72, applied topically twice daily 10% N-acetyl-L-tyrosine ethyl ester cream to her right forearm for four weeks. After four weeks her untreated left forearm was still loose, relatively thin and wrinkled when lifted. In contrast, her right forearm was more firm, smooth, plump and minimally wrinkled when lifted. While there was no change in skin thickness of her left forearm, her right forearm had increased 34% in skin thickness as measured by the micrometer calipers. This result indicated that N-acetyl-tyrosine ethyl ester would be therapeutically effective for topical treatment of wrinkles and changes of skin, nail or hair associated with aging.

17. Effect of N-acetyl-L-arginine on Skin

A female subject, age 72, applied topically twice daily 10% N-acetyl-L-arginine cream to her left forearm for four weeks. After four weeks her untreated right forearm was still loose, relatively thin and wrinkled when lifted. In contrast, her left forearm was more firm, smooth, plump and minimally wrinkled when lifted. While there was no change in skin thickness of her right forearm, her left forearm had increased 22% in skin thickness as measured by the micrometer calipers. This result indicated that N-acetyl-arginine would be therapeutically effective for topical treatment of wrinkles and changes of skin, nail or hair associated with aging.

18. Effect of Combination Composition on Skin

A female subject, age 72, applied topically twice daily a combination cream formulated from 10% each of N-acetyl-α-D-glucosamine and gluconolactone to her right forearm for three weeks. After three weeks her untreated left forearm was still loose, relatively thin and wrinkled when lifted. In contrast, her right forearm was more firm, smooth, plump and minimally wrinkled when lifted. While there was no change in skin thickness of her left forearm, her right forearm had increased 118% in skin thickness as measured by the micrometer calipers. This result indicated that N-acetyl-glucosamine in combination with other topical agents would be topically effective for various cosmetic and dermatologic indications including wrinkles and changes of skin, nail and hair associated with intrinsic and extrinsic aging.

19. Effect of N-acetylamino Acid on the Scalp

A typical composition suitable for topical use on hair, scalp, nail and skin comprising for example N-acetylamino acid may be formulated as follows. N-Acetyl-DL-proline 2 g was dissolved in 98 ml solution prepared from water 40 ml, ethanol 40 ml and propylene glycol 20 ml. The composition with pH 2.7 contained 2% N-acetyl-DL-proline. A male subject, age 66, having itchy scalp topically applied the above composition to itchy area of scalp. A few minutes after the topical application, scalp itch disappeared completely and the scalp remained free of itch for the next 24 hours.

20. Effect of Combination Composition (Anti-fungal Agent) on Nail or Scalp

A typical composition comprising for example N-acetylamino acid in combination with an anti-fungal agent for nail or scalp infections may be formulated as follows. N-Acetylglycine 2 g was dissolved in 98 ml solution prepared from water 40 ml, ethanol 40 ml and propylene glycol 20 ml. The composition thus prepared contained 2% N-acetylglycine, and was used as a nail or scalp conditioner. For nail or scalp infections, N-acetylglycine 2 g and clotrimazole 2 g were dissolved in 96 ml solution prepared from water 40 ml, ethanol 40 ml and propylene glycol 20 ml. The composition with pH 3.7 contained 2% N-acetylglycine and 2% clotrimazole, and were topically effective for nail or scalp infections.

21. N-acetylamino Shampoo Composition

A typical shampoo composition comprising for example N-acetylamino acid for hair, scalp or body wash may be formulated as follows. N-Acetyl-L-arginine 4 g was dissolved in 20 ml water, and the solution thus obtained was mixed uniformly with 76 g shampoo base. The shampoo composition with pH 6.6 contained 4% N-acetyl-L-arginine 22. Effect N-acetyl-L-lysine on an Oily Scalp N-Acetyl-L-lysine 2 g was dissolved in a 98 ml solution prepared from water 40 ml, ethanol 40 ml and propylene glycol 20 ml. The composition with pH 6.5 contained 2% N-acetyl-L-lysine. A male subject, age 66, having an oily and pruritic scalp topically applied the above composition to the affected area of the scalp, and the area was dried with warm air to remove excess solvents. A few minutes after the topical application, the scalp itch disappeared completely and the scalp remained free of itch the next 12 hours.

23. Effect of N-acetyl-DL-proline on Pruritus

A male subject, age 77, with chronic Grover's Disease (Acantholytic Dermatosis) for approximately one year duration had complained about excruciating pruritus on skin lesions of inflammatory papules which did not respond well to conventional topical anti-inflammatory agents. The subject topically applied N-acetyl-DL-proline 5% in oil-in-water cream to the itchy lesions. A few minutes after the topical application, the severe itch disappeared completely and the lesions remained free of itch for the next 12 hours.

24. Effect of N-acetyl-D-galactosamine on Urticaria

A female subject, age 72, having acute urticaria due to unknown cause did not respond to conventional topical anti-itch medications, The subject topically applied N-acetyl-D-galactosamine 5% in solution to skin areas of the urticarial lesions. A few minutes after the topical application, the severe itch disappeared completely and the skin remained free of itch for the next 24 hours with concomitant disappearance of urticarial lesions.

25. Effect of N-acetyl-DL-proline on Itchy Skin and Dry Skin Lesions

A female subject, age 86, with chronic nummular eczema and pruritic dry skin topically applied N-acetyl-DL-proline 5% in solution to itchy skin areas of eczema and dry skin lesions. A few minutes after the topical application, the itch disappeared completely and the lesions remained free of itch for the next 48 hours.

26. Effect of N-acetyl-DL-proline on Itchy Skin

A male subject, age 76, having axillary itch due to use of a conventional antiperspirant topically applied N-acetyl-DL-proline 5% in solution to itchy underarm skin areas. Within a few minutes after the topical application, the itch disappeared completely and the skin remained free of itch for the next five days.

27. Effect of N-acetyl-L-glutamine on Pruritus

A male subject, age 77, with chronic Grover's Disease (Acantholytic Dermatosis) for approximately one year duration had complained about excruciating pruritus on skin lesions of inflammatory papules which did not respond well to conventional topical anti-inflammatory agents. The subject topically applied N-acetyl-L-glutamine 5% in a solution prepared from water 4 parts, ethanol 4 parts and propylene glycol 2 parts by volume. A few minutes after the topical application, the severe itch disappeared completely and the lesions remained free of itch for the next 24 hours.

28. Effect of N-acetyl-α-D-glucosamine on Pruritus

A male subject, age 77, with chronic Grover's Disease (Ancantholytic Dermatosis) for approximately one year duration had complained about excruciating pruritus on skin lesions of inflammatory papules which did not respond well to conventional topical anti-inflammatory agents. The subject topically applied N-acetyl-α-D-glucosamine 5% in a solution prepared from water 4 parts, ethanol 4 parts and propylene glycol 2 parts by volume. A few minutes after the topical application, the severe itch disappeared completely and the lesions remained free of itch for the next 24 hours.

The invention described herein may be embodied in other specific forms without departing from the spirit or essential characteristics thereof. The specific embodiments previously described are therefore to be considered as illustrative of, and not limiting, the scope of the invention. Additionally, the disclosure of all publications cited above are expressly incorporated herein by reference in their entireties to the same extent as if each were incorporated by reference individually.

We claim:

[1. A composition comprising (A) a pharmaceutically acceptable vehicle for topical treatment of cosmetic conditions or dermatological disorders and (B) a therapeutically effective amount of at least one compound selected from the group consisting of N-acetyl aldosamines, N-acetylamino acids, and isomeric or nonisomeric, free acid, salt, lactone, amide, or ester forms thereof, wherein said N-acetyl aldosamine has the formula:

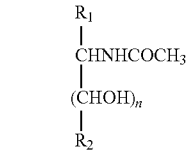

$$R_2(CHOH)_n(CHNHCOCH_3)R_1$$

wherein n is an integer; $R_1$ is selected from the group consisting of CHO, $CONH_2$, and $COOR_3$; $R_2$ is selected from the group consisting of H, I, F, Cl, Br, and an alkyl, alkoxyl, aralkyl or aryl group of saturated or unsaturated, straight or branched chain or cyclic form having 1 to 19 carbon atoms; $R_3$ is selected from the group consisting of H and an alkyl, aralkyl, or aryl group having from 1 to 9 carbon atoms, wherein said N-acetylamino acid or isomeric or nonisomeric, free acid, salt, lactone, amide, or ester form thereof is at least one member selected from the group consisting of N-acetylglycine, N-acetyl-alanine, N-acetyl-valine, N-acetyl-leucine, N-acetyl-isoleucine, N-acetyl-serine, N-acetyl-threonine, N-acetyl-tyrosine, N-acetyl-methionine, N-acetyl-aspartic acid, N-acetyl-asparagine, N-acetyl-glutamine, N-acetyl-arginine, N-acetyl-lysine, N-acetyl-histidine, N-acetyl-phenylalanine, N-acetyl-tyrosine, N-acetyl-tryptophan, N-acetyl-β-alanine, N-acetyl-taurine, N-acetyl-r-aminobutanoic acid, N-acetyl-hydroxyproline, N-acetyl-canavanine, N-acetyl-hydroxylysine, N-acetyl-cycloserine, N-acetyl-homoarginine, N-acetyl-norleucine, N-acetyl-norvaline, N-acetyl-homoserine, N-acetyl-methylserine, N-acetyl-hydroxyvaline, N-acetyl-ethionine, N-acetyl-methoxinine, N-acetyl-β-aminoisobutanoic acid, N-acetyl-homocysteine, N-acetyl-cysteine sulfinic acid, N-acetyl-homophenylalanine, N-acetyl-homotryptophan, N-acetyl-5-hydroxytryptamine (N-acetyl-serotonin), N-acetyltryptamine, N-acetyl-ornithine, N-acetyl-citrulline, N-acetyl-argininosuccinic acid, N-acetyl-dopa, N-acetyl-3-iodotyrosine, N-acetyl-3,5-diiodotyrosine, N-acetyl-3,5,3'-triiodothyronine, N-acetyl-thyroxine, N-acetyl-creatine, N-acetyl-creatinine, N-acetyl-cystine, N-acetyl-homocystine, and isomeric or nonisomeric, free acid, salt, lactone, amide, or ester forms thereof, and N-acetyl-glutamic acid and isomeric or nonisomeric, free acid, lactone, amide, or ester forms thereof.]

[2. The composition of claim 1, wherein said N-acetyl aldosamine or isomeric or nonisomeric, free acid, salt, lactone, amide, or ester form thereof is at least one member selected from the group consisting of N-acetyl-glycerosamine, N-acetyl-erythrosamine, N-acetyl-threosamine, N-acetyl-ribosamine, N-acetyl-arabinosamine, N-acetyl-xylosamine, N-acetyl-lyxosamine, N-acetyl-allosamine, N-acetyl-altrosamine, N-acetyl-glucosamine, N-acetyl-mannosamine, N-acetyl-gulosamine, N-acetyl-idosamine, N-acetyl-galactosamine, N-acetyl-talosamine, N-acetyl-glucoheptosamine, N-acetyl-galactoheptosamine, N-acetyl-mannoheptosamine, N-acetyllactosamine, N-acetylmuramic acid, N-acetylneuramine, N-acetylneuramin Lactose, N-acetyl-glyceraminic acid, N-acetyl-erythrosaminic acid, N-acetyl-threosaminic acid, N-acetyl-ribosaminic acid, N-acetyl-arabinosaminic acid, N-acetyl-xylosaminic acid, N-acetyl-lyxosaminic acid, N-acetyl-allosaminic acid, N-acetyl-altrosaminic acid, N-acetyl-glucosaminic acid, N-acetyl-mannosaminic acid, N-acetyl-gulosaminic acid, N-acetyl-idosaminic acid, N-acetyl-galactosaminic acid, N-acetyl-talosaminic acid, N-acetyl-heptoglucosaminic acid, N-acetyl-heptogalactosaminic acid, N-acetyl-heptomannosaminic acid, N-acetyl-N-acetylneuraminic acid, and isomeric or nonisomeric, free acid, salt, lactone, amide, or ester forms thereof.]

[3. The composition of claim 1, wherein said cosmetic conditions and dermatological disorders are selected from the group consisting of disturbed keratinization, defective syntheses of dermal components, and changes associated with aging of skin, nail and hair, conditions and disorders which include dryness or loose of skin, nail and hair, xerosis, ichthyosis, palmar hyerperkeratoses, plantar hyperkeratoses, uneven and rough surfaces of skin, nail and hair, dandruff, Darier's disease, lichen simplex chronicus, keratoses, acne, pseudofolliculitis barbae, eczema, psoriasis, pruritus, warts, herpes, age spots, lentigines, melasmas, blemished skin, hyperkeratoses, hyperpigmented skin, abnormal or diminished syntheses of collagen, glycosaminoglycans, proteoglycans and elastin as well as diminished levels of such components in the dermis, stretch marks, skin lines, fine lines, wrinkles, thinning of skin, nail plate and hair, skin thickening due to elastosis of photoaging, loss or reduction of skin, nail and hair resiliency, elasticity and recoilability, lack of skin, nail and hair lubricants and luster, dull and older-looking skin, nails and hair, and fragility and splitting of nails and hair.]

[4. A composition comprising:

(A) a pharmaceutically acceptable vehicle for topical treatment of cosmetic conditions or dermatological disorders, (B) a therapeutically effective amount of at least one compound selected from the group consisting of N-acetyl aldosamines, N-acetylamino acids, and isomeric or nonisomeric, free acid, salt, lactone, amide, or ester forms thereof, wherein said N-acetyl aldosamine has the formula:

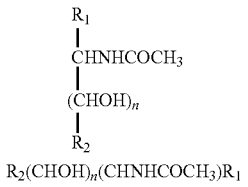

$R_2(CHOH)_n(CHNHCOCH_3)R_1$ wherein n is an integer; $R_1$ is selected from the group consisting of CHO, $CONH_2$, and $COOR_3$; $R_2$ is selected from the group consisting of H, I, F, Cl, Br, and an alkyl, alkoxyl, aralkyl or aryl group of saturated or unsaturated, straight or branched chain or cyclic form having 1 to 19 carbon atoms; $R_3$ is selected from the group consisting of H and an alkyl, aralkyl, or aryl group having from 1 to 9 carbon atoms, wherein said N-acetylamino acid has the formula:

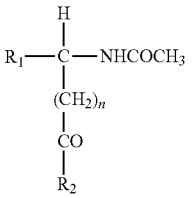

$R_1CH(NHCOCH_3)(CH_2)_nCOR_2$ wherein $R_1$ is H or an alkyl or aralkyl group having 1 to 14 carbon atoms; n is an integer; $R_2$ is OH, $NH_2$ or $OR_3$; and $R_3$ is an alkyl, aralkyl or aryl group having 1 to 9 carbon atoms which may be saturated or unsaturated, straight or branched chain or cyclic form; H attached to a carbon atom may be substituted by I, F, Cl, Br or an alkoxyl group having 1 to 9 carbons; and $R_1$ may carry OH, SH, $SCH_3$, COOH, $NH_2$, $CONH_2$, guanidine or heterocyclic group, and wherein said N-acetylamino acid is not N-acetylcysteine or a derivative thereof, and (C) a cosmetic, pharmaceutical or other topical agent.]

[5. The composition of claim 4, wherein said N-acetyl aldosamine or isomeric or nonisomeric, free acid, salt, lactone, amide, or ester form thereof is at least one member selected from the group consisting of N-acetyl-glycerosamine, N-acetyl-erythrosamine, N-acetyl-threosamine, N-acetyl-ribosamine, N-acetyl-arabinosamine, N-acetyl-xylosamine, N-acetyl-lyxosamine, N-acetyl-allosamine, N-acetyl-altrosamine, N-acetyl-glucosamine, N-acetyl-mannosamine, N-acetyl-gulosamine, N-acetyl-idosamine, N-acetyl-galactosamine, N-acetyl-talosamine, N-acetyl-glucoheptosamine, N-acetyl-galactoheptosamine, N-acetyl-mannoheptosamine, N-acetyllactosamine, N-acetylmuramic acid, N-acetylneuramine, N-acetylneuramin Lactose, N-acetyl-glyceraminic acid, N-acetyl-erythrosaminic acid, N-acetyl-threosaminic acid, N-acetyl-ribosaminic acid, N-acetyl-arabinosaminic acid, N-acetyl-xylosaminic acid, N-acetyl-lyxosaminic acid, N-acetyl-allosaminic acid, N-acetyl-altrosaminic acid, N-acetyl-glucosaminic acid, N-acetyl-mannosaminic acid, N-acetyl-gulosaminic acid, N-acetyl-idosaminic acid, N-acetyl-galactosaminic acid, N-acetyl-talosaminic acid, N-acetyl-heptoglucosaminic acid, N-acetyl-heptogalactosaminic acid, N-acetyl-heptomannosaminic acid, N-acetyl-N-acetylneuraminic acid, and isomeric or nonisomeric, free acid, salt, lactone, amide, or ester forms thereof.]

[6. The composition of claim 4 wherein said N-acetylamino acid or isomeric or nonisomeric, free acid, salt, lactone, amide, or ester form thereof is at least one member selected from the group consisting of N-acetyl-glycine, N-acetyl-alanine, N-acetyl-valine, N-acetyl-leucine, N-acetyl-isoleucine, N-acetyl-serine, N-acetyl-threonine, N-acetyl-tyrosine, N-acetyl-methionine, N-acetyl-aspartic acid, N-acetyl-asparagine, N-acetyl-glutamic acid, N-acetyl-glutamine, N-acetyl-argininc, N-acetyl-lysine, N-acetyl-histidine, N-acetyl-phenylalanine, N-acetyl-tyrosine, N-acetyl-tryptophan, N-acetyl-proline, N-acetyl-β-alanine, N-acetyl-taurine, N-acetyl-r-aminobutanoic acid, N-acetyl-hydroxyproline, N-acetyl-canavanine, N-acetyl-hydroxylysine, N-acetyl-cycloserine, N-acetyl-homoarginine, N-acetyl-norleucine, N-acetyl-norvaline, N-acetyl-homoserine, N-acetyl-methylserine, N-acetyl-hydroxyvaline, N-acetyl-ethionine, N-acetyl-methoxinine, N-acetyl-β-aminoisobutanoic acid, N-acetyl-homocysteine, N-acetyl-cysteine sulfinic acid, N-acetyl-homophenylalanine, N-acetyl-homotryptophan, N-acetyl-5-hydroxytryptamine (N-acetylserotonin), N-acetyltryptamine, N-acetyl-ornithine, N-acetyl-citrulline, N-acetyl-argininosuccinic acid; N-acetyl-dopa, N-acetyl-3-iodotyrosine, N-acetyl-3,5-diiodotyrosine, N-acetyl-3,5,3'-triiodothyronine, N-acetyl-thyroxine, N-acetyl-creatine, N-acetyl-creatinine, N-acetyl-cystine, N-acetyl-homocystine, and or isomeric or nonisomeric, free acid, salt, lactone, amide, or ester forms thereof.]

[7. The composition of claim 4, wherein said cosmetic conditions and dermatological disorders are selected from the group consisting of disturbed keratinization, defective syntheses of dermal components, and changes associated with aging of skin, nail and hair, conditions and disorders which include dryness or loose of skin, nail and hair, xerosis, ichthyosis, palmar hyerperkeratoses, plantar hyperkeratoses, uneven and rough surfaces of skin, nail and hair, dandruff, Darier's disease, lichen simplex chronicus, keratoses, acne, pseudofolliculitis barbae, eczema, psoriasis, pruritus, warts, herpes, age spots, lentigines, melasmas, blemished skin, hyperkeratoses, hyperpigmented skin, abnormal or diminished syntheses of collagen, glycosaminoglycans, proteoglycans and elastin as well as diminished levels of such components in the dermis, stretch marks, skin lines, fine lines, wrinkles, thinning of skin, nail plate and hair, skin thickening due to elastosis of photoaging, loss or reduction of skin, nail and hair resiliency, elasticity and recoilability, lack of skin, nail and hair lubricants and luster, dull and older-looking skin, nails and hair, and fragility and splitting of nails and hair.]

[8. The composition of claim 4, wherein said cosmetic, pharmaceutical, or other topical agent is selected from the group consisting of agents that improve or eradicate age spots, keratoses and wrinkles, local analgesics and anesthetics, antiacne agents, antibacterials, antiyeast agents, antifungal agents, antiviral agents, antidandruff agents, antidermatitis agents, antihistamine agents, antipruritic agents, antiemetics, antimotion sickness agents, antiinflammatory agents, antihyperkeratolytic agents, antiperspirants, antipsoriatic agents, antiseborrheic agents, hair conditioners and hair treatment agents, antiaging and antiwrinkle agents, sunblock and sunscreen agents, skin lightening agents, depigmenting agents, vitamins, corticosteroids, tanning agents, hormones, retinoids, and topical cardiovascular agents.]

[9. The composition of claim 8, wherein said cosmetic, pharmaceutical, or other topical agent is selected from the group consisting of clotrimazole, ketoconazole, miconazole, griseofulvin, econazole, metronidazole, hydroxyzine, diphenhydramine, pramoxine, lidocaine, procaine, mepivacaine, monobenzone, erythromycin, tetracycline, clindamycin, meclocycline, hydroquinone, hydroquinone monoether, minocycline, naproxen, ibuprofen, theophylline, cromolyn, albuterol, retinol, retinyl acetate, retinyl palmitate, retinoic acid, 13-cis retinoic acid, hydrocortisone, hydrocortisone 21-acetate, hydrocortisone 17-valerate, hydrocortisone 17-butyrate, betamethasone valerate, betamethasone dipropionate, triamcinolone acetonide, fluocinonide, clobetasol propionate, benzoyl peroxide, crotamiton, propranolol, promethazine, salicylic acid, vitamin E and vitamin E acetate.]

[10. A composition comprising (A) a pharmaceutically acceptable vehicle for topical treatment of cosmetic conditions or dermatological disorders and (B) at least 1% by total weight of the composition of at least one compound selected from the group consisting of N-acetyl aldosamines, N-acetylamino acids, and isomeric or nonisomeric, free acid, salt, lactone, amide, or ester forms thereof, wherein said N-acetyl aldosamine has the formula:

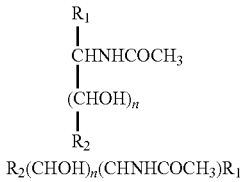

wherein n is an integer; $R_1$ is selected from the group consisting of CHO, $CONH_2$, and $COOR_3$; $R_2$ is selected from the group consisting of H, I, F, Cl, Br, and an alkyl, alkoxyl, aralkyl or aryl group of saturated or unsaturated, straight or branched chain or cyclic form having 1 to 19 carbon atoms; $R_3$ is selected from the group consisting of H and an alkyl, aralkyl, or aryl group having from 1 to 9 carbon atoms, wherein said N-acetylamino acid or isomeric or nonisomeric, free acid, salt, lactone, amide, or ester form thereof is at least one member selected from the group consisting of N-acetyl-glycine, N-acetyl-alanine, N-acetyl-valine, N-acetyl-leucine, N-acetyl-isoleucine, N-acetyl-serine, N-acetyl-threonine, N-acetyl-tyrosine, N-acetyl-methionine, N-acetyl-aspartic acid, N-acetyl-asparagine, N-acetyl-glutamine, N-acetyl-arginine, N-acetyl-lysine, N-acetyl-histidine, N-acetyl-phenylalanine, N-acetyl-tyrosine, N-acetyl-tryptophan, N-acetyl-proline, N-acetyl-β-alanine, N-acetyl-taurine, N-acetyl-r-aminobutanoic acid, N-acetyl-hydroxyproline, N-acetyl-canavanine, N-acetyl-hydroxylysine, N-acetyl-cycloserine, N-acetyl-homoarginine, N-acetyl-norleucine, N-acetyl-norvaline, N-acetyl-homoserine, N-acetyl-methylserine, N-acetyl-hydroxyvaline, N-acetyl-ethionine, N-acetyl-methoxinine, N-acetyl-β-aminoisobutanoic acid, N-acetyl-homocysteine, N-acetyl-cysteine sulfinic acid, N-acetyl-homophenylalanine, N-acetyl-homotryptophan, N-acetyl-5-hydroxytryptamine (N-acetylserotonin), N-acetyltryptamine, N-acetyl-ornithine, N-acetyl-citrulline, N-acetyl-argininosuccinic acid, N-acetyl-dopa, N-acetyl-3-iodotyrosine, N-acetyl-3,5-diiodotyrosine, N-acetyl-3,5,3'-triiodothyronine, N-acetyl-thyroxine, N-acetyl-creatine, N-acetyl-creatinine, N-acetyl-cystine, N-acetyl-homocystine, and isomeric or nonisomeric, free acid, salt, lactone, amide, or ester forms thereof, and N-acetyl glutamic acid and isomeric or nonisomeric, free acid, lactone, amide, or ester forms thereof.]

[11. A composition comprising:

(A) a pharmaceutically acceptable vehicle for topical treatment of cosmetic conditions or dermatological disorders, (B) at least 1% by total weight of the composition of at least one compound selected from the group consisting of N-acetyl aldosamines, N-acetylamino acids, and isomeric or nonisomeric, free acid, salt, lactone, amide, or ester forms thereof, wherein said N-acetyl aldosamine has the formula:

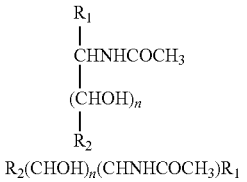

$R_2(CHOH)_n(CHNHCOCH_3)R_1$ wherein n is an integer; $R_1$ is selected from the group consisting of CHO, $CONH_2$, and $COOR_3$; $R_2$ is selected from the group consisting of H, I, F, Cl, Br, and an alkyl, alkoxyl, aralkyl or aryl group of saturated or unsaturated, straight or branched chain or cyclic form having 1 to 19 carbon atoms; $R_3$ is selected from the group consisting of H and an alkyl, aralkyl, or aryl group having from 1 to 9 carbon atoms, wherein said N-acetylamino acid is N-acetyl-proline or has the formula:

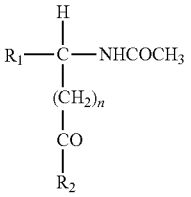

$R_1CH(NHCOCH_3)(CH_2)_nCOR_2$ wherein $R_1$ is H or an alkyl or aralkyl group having 1 to 14 carbon atoms; n is an integer; $R_2$ is OH, $NH_2$ or $OR_3$; and $R_3$ is an alkyl, aralkyl or aryl group having 1 to 9 carbon atoms which may be saturated or unsaturated, straight or branched chain or cyclic form; H attached to a carbon atom may be substituted by I, F, Cl, Br or an alkoxyl group having 1 to 9 carbons; and $R_1$ may carry OH, SH, $SCH_3$, COOH, $NH_2$, $CONH_2$, guanidine or heterocyclic group, and wherein said N-acetylamino acid is not N-acetylcysteine or a derivative thereof, and (C) a cosmetic, pharmaceutical or other topical agent.]

[12. A method for treating cosmetic conditions and dermatological disorders comprising topically applying a composition comprising (A) a pharmaceutically acceptable vehicle for topical treatment of cosmetic conditions or dermatological disorders and (B) a therapeutically effective amount of a composition comprising at least one compound selected from the group consisting of N-acetyl aldosamines, N-acetylamino acids and isomeric or nonisomeric, free acid, salt, lactone, amide, or ester forms thereof, wherein said N-acetyl aldosamine has the formula:

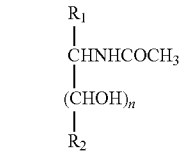

$R_2(CHOH)_n(CHNHCOCH_3)R_1$ wherein n is an integer; $R_1$ is selected from the group consisting of CHO, $CONH_2$, and $COOR_3$; $R_2$ is selected from the group consisting of H, I, F, Cl, Br, and an alkyl, alkoxyl, aralkyl or aryl group of saturated or unsaturated, straight or branched chain or cyclic form having 1 to 19 carbon atoms; $R_3$ is selected from the group consisting of H and an alkyl, aralkyl or aryl group having from 1 to 9 carbon atoms, and wherein said N-acetylamino acid or isomeric or nonisomeric, free acid, salt, lactone, amide, or ester form thereof is at least one member selected from the group consisting of N-acetyl-glycine, N-acetyl-alanine, N-acetyl-valine, N-acetyl-leucine, N-acetyl-isoleucine, N-acetyl-serine, N-acetyl-threonine, N-acetyl-tyrosine, N-acetyl-cysteine, N-acetyl-methionine, N-acetyl-aspartic acid, N-acetyl-asparagine, N-acetyl-glutamine, N-acetyl-arginine, N-acetyl-lysine, N-acetyl-histidine, N-acetyl-phenylalanine, N-acetyl-tyrosine, N-acetyl-tryptophan, N-acetyl-proline, N-acetyl-β-alanine, N-acetyl-taurine, N-acetyl-r-aminobutanoic acid, N-acetyl-hydroxyproline, N-acetyl-canavanine, N-acetyl-hydroxylysine, N-acetyl-cycloserine, N-acetyl-homoarginine, N-acetyl-norleucine, N-acetyl-norvaline, N-acetyl-homoserine, N-acetyl-methylserine, N-acetyl-hydroxyvaline, N-acetyl-ethionine, N-acetyl-methoxinine, N-acetyl-β-aminoisobutanoic acid, N-acetyl-homocysteine, N-acetyl-cysteine sulfinic acid, N-acetyl-homophenylalanine, N-acetyl-homotryptophan, N-acetyl-5-hydroxytryptamine (N-acetylserotonin), N-acetyltryptamine, N-acetyl-ornithine, N-acetyl-citrulline, N-acetyl-argininosuccinic acid, N-acetyl-dopa, N-acetyl-3-iodotyrosine, N-acetyl-3,5-diiodotyrosine, N-acetyl-3,5,3'-triiodothyronine, N-acetyl-thyroxine, N-acetyl-creatine, N-acetyl-creatinine, N-acetyl-cystine, N-acetyl-homocystine, and isomeric or nonisomeric, free acid, salt lactone, amide, or ester forms thereof, and N-acetyl-glutamic acid and isomeric or nonisomeric, free acid, lactone, amide, or ester forms thereof.]

[13. The method of claim 12, wherein said N-acetyl aldosamine or isomeric or nonisomeric, free acid, salt, lactone, amide, or ester form thereof is at least one member selected from the group consisting of N-acetyl-glycerosamine, N-acetyl-erythrosamine, N-acetyl-threosamine, N-acetyl-ribosamine, N-acetyl-arabinosamine, N-acetyl-xylosamine, N-acetyl-lyxosamine, N-acetyl-allosamine, N-acetyl-altrosamine, N-acetyl-glucosamine, N-acetyl-mannosamine, N-acetyl-gulosamine, N-acetyl-idosamine, N-acetyl-galactosamine, N-acetyl-talosamine, N-acetyl-glucoheptosamine, N-acetyl-galactoheptosamine, N-acetyl-mannoheptosamine, N-acetyllactosamine, N-acetylmuramic acid, N-acetylneuramine, N-acetylneuramin Lactose, N-acetyl-glyceraminic acid, N-acetyl-erythrosaminic acid, N-acetyl-threosaminic acid, N-acetyl-ribosaminic acid, N-acetyl-arabinosaminic acid, N-acetyl-xylosaminic acid, N-acetyl-lyxosaminic acid, N-acetyl-allosaminic acid, N-acetyl-altrosaminic acid, N-acetyl-glucosaminic acid, N-acetyl-mannosaminic acid, N-acetyl-gulosaminic acid, N-acetyl-idosaminic acid, N-acetyl-galactosaminic acid, N-acetyl-talosaminic acid, N-acetyl-heptoglucosaminic acid, N-acetyl-heptogalactosaminic acid, N-acetyl-heptomannosaminic acid, N-acetyl-N-acetylneuraminic acid, and isomeric or nonisomeric, free acid, salt, lactone, amide, or ester forms thereof.]

[14. The method of claim 12, wherein said cosmetic conditions and dermatological disorders are selected from the group consisting of disturbed keratinization, defective syntheses of dermal components, and changes associated with aging of skin, nail and hair, conditions and disorders which include dryness or loose of skin, nail and hair, xerosis, ichthyosis, palmar hyerperkeratoses, plantar hyperkeratoses, uneven and rough surfaces of skin, nail and hair, dandruff, Darier's disease, lichen simplex chronicus, keratoses, acne, pseudofolliculitis barbae, eczema, psoriasis, pruritus, warts, herpes, age spots, lentigines, melasmas, blemished skin, hyperkeratoses, hyperpigmented skin, abnormal or diminished syntheses of collagen, glycosaminoglycans, proteoglycans and elastin as well as diminished levels of such components in the dermis, stretch marks, skin lines, fine lines, wrinkles, thinning of skin, nail plate and hair, skin thickening due to elastosis of photoaging, loss or reduction of skin, nail and hair resiliency, elasticity and recoilability, lack of skin, nail and hair lubricants and luster, dull and older-looking skin, nails and hair, and fragility and splitting of nails and hair.]

[15. A method for treating cosmetic conditions and dermatological disorders comprising topically applying a composition comprising:

(A) a pharmaceutically acceptable vehicle for topical treatment of cosmetic conditions or dermatological disorders, (B) a therapeutically effective amount of at least one compound selected from the group consisting of N-acetyl aldosamines, N-acetylamino acids, and isomeric or nonisomeric, free acid, salt, lactone, amide, or ester forms thereof, wherein said N-acetyl aldosamine has the formula:

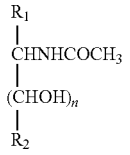

$R_2(CHOH)_n(CHNHCOCH_3)R_1$ wherein n is an integer; $R_1$ is selected from the group consisting of CHO, $CONH_2$, and $COOR_3$; $R_2$ is selected from the group consisting of H, I, F, Cl, Br, and an alkyl, alkoxyl, aralkyl or aryl group of saturated or unsaturated, straight or branched chain or cyclic form having 1 to 19 carbon atoms; $R_2$ is selected from the group consisting of H and an alkyl, aralkyl, or aryl group having from 1 to 9 carbon atoms, wherein said N-acetylamino acid is N-acetyl-proline or has the formula:

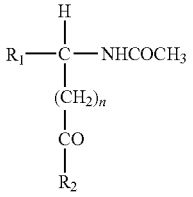

$R_1CH(NHCOCH_3)(CH_2)_nCOR_2$ wherein $R_1$ is H or an alkyl or aralkyl group having 1 to 14 carbon atoms; n is an integer; $R_2$ is OH, $NH_2$ or $OR_3$; and $R_3$ is an alkyl, aralkyl or aryl group having 1 to 9 carbon atoms which may be saturated or unsaturated, straight or branched chain or cyclic form; H attached to a carbon atom may be substituted by I, F, Cl, Br or an alkoxyl group having 1 to 9 carbons; and $R_1$ may carry OH, SH, $SCH_3$, COOH, $NH_2$, $CONH_2$, guanidine or heterocyclic group, and wherein said N-acetylamino acid is not N-acetylcysteine or a derivative thereof, and (C) a cosmetic, pharmaceutical or other topical agent.]

[16. The method of claim 15, wherein said N-acetyl aldosamine or isomeric or nonisomeric, free acid, salt, lactone, amide, or ester form thereof is at least one member selected from the group consisting of N-acetyl-glycerosamine, N-acetyl-erythrosamine, N-acetyl-threosamine, N-acetyl-ribosamine, N-acetyl-arabinosamine, N-acetyl-xylosamine, N-acetyl-lyxosamine, N-acetyl-allosamine, N-acetyl-altrosamine, N-acetyl-glucosamine, N-acetyl-mannosamine, N-acetyl-gulosamine, N-acetyl-idosamine, N-acetyl-galactosamine, N-acetyl-talosamine, N-acetyl-glucoheptosamine, N-acetyl-galactoheptosamine, N-acetyl-mannoheptosamine, N-acetyllactosamine, N-acetylmuramic acid, N-acetylneuramine, N-acetylneuramin Lactose, N-acetyl-glyceraminic acid, N-acetyl-erythrosaminic acid, N-acetyl-threosaminic acid, N-acetyl-ribosaminic acid, N-acetyl-arabinosaminic acid, N-acetyl-xylosaminic acid, N-acetyl-lyxosaminic acid, N-acetyl-allosaminic acid, N-acetyl-altrosaminic acid, N-acetyl-glucosaminic acid, N-acetyl-mannosaminic acid, N-acetyl-gulosaminic acid, N-acetyl-idosaminic acid, N-acetyl-galactosaminic acid, N-acetyl-talosaminic acid, N-acetyl-heptoglucosaminic acid, N-acetyl-heptogalactosaminic acid, N-acetyl-heptomannosaminic acid, N-acetyl-N-acetylneuraminic acid, and isomeric or nonisomeric, free acid, salt, lactone, amide, or ester forms thereof.]

[17. The method of claim 15, wherein said N-acetylamino acid or isomeric or nonisomeric, free acid, salt, lactone, amide, or ester form thereof is at least one member selected from the group consisting of N-acetyl-glycine, N-acetyl-alanine, N-acetyl-valine, N-acetyl-leucine, N-acetyl-isoleucine, N-acetyl-serine, N-acetyl-threonine, N-acetyl-tyrosine, N-acetyl-methionine, N-acetyl-aspartic acid, N-acetyl-asparagine, N-acetyl-glutamic acid, N-acetyl-glutamine, N-acetyl-arginine, N-acetyl-lysine, N-acetyl-histidine, N-acetyl-phenylalanine, N-acetyl-tyrosine, N-acetyl-tryptophan, N-acetyl-proline, N-acetyl-β-alanine, N-acetyl-taurine, N-acetyl-r-aminobutanoic acid, N-acetyl-hydroxyproline, N-acetyl-canavanine, N-acetyl-hydroxylysine, N-acetyl-cycloserine, N-acetyl-homoarginine, N-acetyl-norleucine, N-acetyl-norvaline, N-acetyl-homoserine, N-acetyl-methylserine, N-acetyl-hydroxyvaline, N-acetyl-ethionine, N-acetyl-methoxinine, N-acetyl-β-aminoisobutanoic acid, N-acetyl-homocysteine, N-acetyl-cysteine sulfinic acid, N-acetyl-homophenylalanine, N-acetyl-homotryptophan, N-acetyl-5-hydroxytryptamine (N-acetylserotonin), N-acetyltryptamine, N-acetyl-ornithine, N-acetyl-citrulline, N-acetyl-argininosuccinic acid, N-acetyl-dopa, N-acetyl-3-iodotyrosine, N-acetyl-3,5-diiodotyrosine, N-acetyl-3,5,3'-triiodothyronine, N-acetyl-thyroxine, N-acetyl-creatine, N-acetyl-creatinine, N-acetyl-cystine, N-acetyl-homocystine, and isomeric or nonisomeric, free acid, salt, lactone, amide, or ester forms thereof.]

[18. The method of claim 15, wherein said cosmetic conditions and dermatological disorders are selected from the groups consisting of disturbed keratinization, defective syntheses of dermal components, and changes associated with aging of skin, nail, and hair, conditions and disorders which include dryness or loose of skin, nail and hair, xerosis, ichthyosis, palmar hyerperkeratoses, plantar hyperkeratoses, uneven and rough surfaces of skin, nail and hair, dandruff, Darier's disease, lichen simplex chronicus, keratoses, acne, pseudofolliculitis barbae, eczema, psoriasis, pruritus, warts, herpes, age spots, lentigines, melasmas, blemished skin, hyperkeratoses, hyperpigmented skin, abnormal or diminished syntheses of collagen, glycosaminoglycans, proteoglycans and elastin as well as diminished levels of such components in the dermis, stretch marks, skin lines, fine lines, wrinkles, thinning of skin, nail plate and hair, skin thickening due to elastosis of photoaging, loss or reduction of skin, nail and hair resiliency, elasticity and recoilability, lack of skin, nail and hair lubricants and luster, dull and older-looking skin, nails and hair, and fragility and splitting of nails and hair.]

[19. The method of claim 15, wherein said cosmetic, pharmaceutical, or other topical agent is selected from the group consisting of agents that improve or eradicate age spots, keratoses and wrinkles, local analgesics and anesthetics, antiacne agents, antibacterials, antiyeast agents, antifungal agents, antiviral agents, antidandruff agents, antidermatitis agents, antihistamine agents, antipruritic agents, antiemetics, antimotion sickness agents, antiinflammatory agents, antihyperkeratolytic agents, antiperspirants, antipsoriatic agents, antiseborrheic agents, hair conditioners and hair treatment agents, antiaging and antiwrinkle agents, sunblock and sunscreen agents, skin lightening agents, depigmenting agents, vitamins, corticosteroids, tanning agents, hormones, retinoids, and topical cardiovascular agents.]

[20. The method of claim 19, wherein said cosmetic, pharmaceutical, or other topical agent is selected from the group consisting of clotrimazole, ketoconazole, miconazole, griseofulvin, econazole, metronidazole, hydroxyzine, diphenhydramine, pramoxine, lidocaine, procaine, mepivacaine, monobenzone, erythromycin, tetracycline, clindamycin, meclocycline, hydroquinone, hydroquinone monoether, minocycline, naproxen, ibuprofen, theophylline, cromolyn, albuterol, retinol, retinyl acetate, retinyl palmitate, retinoic acid, 13-cis retinoic acid, hydrocortisone, hydrocortisone 21-acetate, hydrocortisone 17-valerate, hydrocortisone 17-butyrate, betamethasone valerate, betamethasone dipropionate, triamcinolone acetonide, fluocinonide, clobetasol propionate, benzoyl peroxide, crotamiton, propranolol, promethazine, salicylic acid, vitamin E, and vitamin E acetate.]

*21. A method for treating cosmetic conditions and dermatological disorders comprising topically applying an effective amount of a composition comprising a topically acceptable vehicle and a therapeutically effective amount of at least one compound selected from the group consisting of N-acetyl-arginine, N-acetyl-asparagine, N-acetyl-aspartic acid, N-acetyl-lysine, N-acetyl-tryptophan, N-acetyl-ornithine, as isomeric, non-isomeric, free acid, salt, amide or ester forms thereof; wherein the cosmetic conditions and dermatological disorders are selected from the group consisting of disturbed keratinization, defective syntheses of dermal components, changes associated with aging of skin and nail, conditions and disorders selected from dryness of or looseness of skin and nail, xerosis, ichthyosis, palmar hyperkeratoses, plantar hyperkeratoses, uneven and rough surfaces of skin and nail, Darier's disease, lichen simplex chronicus, keratoses, acne, pseudofolliculitis barbae, eczema, psoriasis, pruritus, age spots, lentigines, melasmas, hyperkeratoses, hyperpigmented skin, abnormal or diminished syntheses of collagen, glycosaminoglycans, proteoglycans and elastin, diminished levels of collagen, glycosaminoglycans, proteoglycans and elastin in the dermis, stretch marks, skin lines, fine lines, wrinkles, thinning of skin and nail plate, skin thickening due to elastosis of photoaging, loss or reduction of skin and nail resiliency, elasticity and recoilability, lack of skin and nail resiliency, elasticity and recoilability, lack of skin, nail and hair lubricants and luster, and fragility and splitting of nails, and to increase the skin thickness.*

*22. The method of claim 21, wherein the compound is selected from the group consisting of N-acetyl-aspartic acid and N-acetyl-lysine.*

*23. The method of claim 21, wherein the cosmetic conditions and dermatological disorders are selected from the group consisting of changes associated with aging of skin, acne, eczema, psoriasis, pruritus, age spots, lentigines, melasmas, hyperpigmented skin, stretch marks, wrinkles, and to increase the skin thickness.*

*24. The method of claim 23, wherein the cosmetic conditions and dermatological disorders are selected from the group consisting of changes associated with aging of skin, eczema, pruritus, age spots, hyperpigmented skin, stretch marks, wrinkles, and to increase the skin thickness.*

*25. The method of claim 21, wherein the composition further comprises a cosmetic, pharmaceutical or other topical agent.*

*26. The method of claim 25, wherein the cosmetic, pharmaceutical or other topical agent is selected from the group consisting of agents that improve or eradicate age spots, keratoses and wrinkles, local analgesics and anesthetics, antiacne agents, antibacterials, antiyeast agents, antifungal agents, antiviral agents, antidermatitis agents, antihistamine agents, antipruritic agents, antiemetics, antimotion sickness agents, antiinflammatory agents, antihyperkeratotic agents, antiperspirants, antipsoriatic agents, antiseborrheic agents, antiaging and antiwrinkle agents, sunblock and sunscreen agents, skin lightening agents, depigmenting agents, vitamins, corticosteroids, tanning agents, hormones, retinoids, and topical cardiovascular agents.*

*27. The method of claim 26, wherein the cosmetic, pharmaceutical or other topical agent is selected from the group consisting of clotrimazole, ketoconazole, miconazole, griseofulvin, econazole, metronidazole, hydroxyzine, diphenhydramine, pramoxine, lidocaine, procaine, mepivacaine, monobenzone, erythromycin, tetracycline, clindamycin, meclocycline, hydroquinone, hydroquinone monoether, minocycline, naproxen, ibuprofen, theophylline, cromolyn, albuterol, retinol, retinyl acetate, retinyl palmitate, retinoic acid, 13-cis retinoic acid, hydrocortisone, hydrocortisone 21-acetate, hydrocortisone 17-valerate, hydrocortisone 17-butyrate, betamethasone valerate, betamethasone dipropionate, triamcinolone acetonide, fluocinonide, clobetasol propionate, benzoyl peroxide, crotamiton, propranolol, promethazine, salicylic acid, vitamin E and vitamin E acetate.*

28. A method for treating cosmetic conditions and dermatological disorders comprising topically applying an effective amount of a composition comprising a topically acceptable vehicle and a therapeutically effective amount of N-acetyl-tyrosine amide as isomeric or non-isomeric forms thereof, wherein the composition does not contain corticosteroids or retinoic acid for synergistic effects;

wherein the cosmetic conditions and dermatological disorders are selected from the group consisting of disturbed keratinization, defective syntheses of dermal components, changes associated with aging of skin and nail, conditions and disorders selected from dryness of or looseness of skin and nail, xerosis, ichthyosis, palmar hyperkeratoses, plantar hyperkeratoses, uneven and rough surfaces of skin and nail, Darier's disease, lichen simplex chronicus, keratoses, acne, pseudofolliculitis barbae, eczema, psoriasis, pruritus, hyperkeratoses, abnormal or diminished syntheses of collagen, glycosaminoglycans, proteoglycans and elastin, diminished levels of collagen, glycosaminoglycans, proteoglycans and elastin in the dermis, stretch marks, skin lines, fine lines, wrinkles; thinning of skin and nail plate; loss or reduction of skin and nail resiliency, elasticity and recoilability; lack of skin and nail resiliency, elasticity and recoilability; lack of skin and nail lubricants and luster; fragility and splitting of nails; and to increase skin thickness.

29. The method of claim 28, wherein the cosmetic conditions and dermatological disorders are selected from the group consisting of changes associated with skin aging, skin lines, fine lines, wrinkles, and to increase skin thickness.

30. The method of claim 28, wherein the composition further comprises a cosmetic, pharmaceutical or other topical agent.

31. The method of claim 30, wherein the cosmetic, pharmaceutical or other topical agent is selected from the group consisting of agents that improve or eradicate keratoses and wrinkles, local analgesics and anesthetics, antiacne agents, antibacterials, antiyeast agents, antifungal agents, antiviral agents, antidermatitis agents, antihistamine agents, antipruritic agents, antiemetics, antimotion sickness agents, antihyperkeratotic agents, antiperspirants, antipsoriatic agents, antiseborrheic agents, antiaging and antiwrinkle agents, sunblock and sunscreen agents, vitamins, hormones, retinoids, and topical cardiovascular agents.

32. The method of claim 31, wherein the cosmetic, pharmaceutical or other topical agent is selected from the group consisting of clotrimazole, ketoconazole, miconazole, griseofulvin, econazole, metronidazole, hydroxyzine, diphenhydramine, pramoxine, lidocaine, procaine, mepivacaine, monobenzone, erythromycin, tetracycline, clindamycin, meclocycline, hydroquinone, hydroquinone monoether, minocycline, naproxen, ibuprofen, theophylline, cromolyn, albuterol, benzoyl peroxide, crotamiton, propranolol, promethazine, salicylic acid, vitamin E and vitamin E acetate.

33. A method for topically treating cosmetic conditions and dermatological disorders of the skin comprising a therapeutically effective amount of N-acetylcysteine as free acid, salt, amide, ester, isomeric or non-isomeric forms thereof, in an anhydrous composition, wherein the cosmetic conditions and dermatological disorders are selected from the group consisting of defective syntheses of dermal components, conditions and disorders selected from looseness of skin, uneven and rough surfaces of skin, pseudofolliculitis barbae, pruritus, abnormal syntheses of collagen, glycosaminoglycans, proteoglycans and elastin, diminished levels of glycosaminoglycans and proteoglycans in the dermis, loss, lack or reduction of skin, resiliency, elasticity and recoilability; and lack of skin lubricants and luster.

34. The method of claim 33, wherein the composition further comprises a cosmetic, pharmaceutical or other topical agent.

35. The method of claim 34, wherein the cosmetic, pharmaceutical or other topical agent is selected from the group consisting of agents that improve or eradicate keratoses, local analgesics and anesthetics, antiacne agents, antibacterials, antiyeast agents, antifungal agents, antiviral agents, antidermatitis agents, antihistamine agents, antipruritic agents, antiemetics, antimotion sickness agents, antiinflammatory agents, antihyperkeratotic agents, antiperspirants, antipsoriatic agents, antiseborrheic agents, antiaging and antiwrinkle agents, sunblock and sunscreen agents, vitamins, corticosteroids, hormones, retinoids, and topical cardiovascular agents.

36. The method of claim 35, wherein the cosmetic or pharmaceutical agent is selected from the group consisting of clotrimazole, ketoconazole, miconazole, griseofulvin, econazole, metronidazole, hydroxyzine, diphenhydramine, pramoxine, lidocaine, procaine, mepivacaine, monobenzone, erythromycin, tetracycline, clindamycin, meclocycline, hydroquinone, hydroquinone monoether, minocycline, naproxen, ibuprofen, theophylline, cromolyn, albuterol, retinol, retinyl acetate, retinyl palmitate, retinoic acid, 13-cis retinoic acid, hydrocortisone, hydrocortisone 21-acetate, hydrocortisone 17-valerate, hydrocortisone 17-butyrate, betamethasone valerate, betamethasone dipropionate, triamcinolone acetonide, fluocinonide, clobetasol propionate, benzoyl peroxide, crotamiton, propranolol, promethazine, salicylic acid, vitamin E and vitamin E acetate.

37. A method for treating cosmetic conditions and dermatological disorders comprising topically applying an effective amount of a composition comprising a topically acceptable vehicle and a therapeutically effective amount of at least one compound selected from the group consisting of N-acetyl-glutamic acid, as isomeric, non-isomeric, amide or ester forms thereof;

wherein the cosmetic conditions and dermatological disorders are selected from the group consisting of defective syntheses of dermal components, changes associated with aging of skin and nail, conditions and disorders selected from ichthyosis, palmar hyperkeratoses, plantar hyperkeratoses, lichen simplex chronicus, keratoses, acne, pseudofolliculitis barbae, eczema, pruritus, age spots, lentigines, melasmas, hyperkeratoses, hyperpigmented skin, abnormal or diminished syntheses of collagen, glycosaminoglycans, proteoglycans and elastin, diminished levels of collagen, glycosaminoglycans, proteoglycans and elastin in the dermis, stretch marks, skin lines, fine lines, wrinkles, thinning of skin and nail plate, skin thickening due to elastosis of photoaging, loss or reduction of skin and nail resiliency, elasticity and recoilability, lack of skin and nail resiliency, elasticity and recoilability, lack of skin and nail lubricants and luster, and fragility and splitting of nails, and to increase the skin thickness.

38. The method of claim 37, wherein the ester form is N-acetyl-glutamic ester.

39. The method of claim 38, wherein the N-acetyl-glutamic ester is selected from the group consisting of N-acetyl-glutamic dimethyl ester, N-acetyl-glutamic diethyl ester, N-acetyl-glutamic dipropyl ester and N-acetyl-glutamic diisopropyl ester.

*40. The method of claim 39, wherein the N-acetyl-glutamic ester is N-acetyl-glutamic diethyl ester, and the cosmetic condition or dermatological disorder is acne.*

*41. The method of claim 37, wherein the composition further comprises a cosmetic, pharmaceutical or other topical agent excluding antipruritic agents.*

*42. The method of claim 41, wherein the cosmetic, pharmaceutical or other topical agent is selected from the group consisting of agents that improve or eradicate age spots, keratoses and wrinkles, local analgesics and anesthetics, antiacne agents, antibacterials, antiyeast agents, antifungal agents, antiviral agents, antidermatitis agents, antihistamine agents, antiemetics, antimotion sickness agents, antiinflammatory agents, antihyperkeratotic agents, antiperspirants, antipsoriatic agents, antiseborrheic agents, antiaging and antiwrinkle agents, sunblock and sunscreen agents, skin lightening agents, depigmenting agents, vitamins, corticosteroids, tanning agents, hormones, retinoids, and topical cardiovascular agents.*

*43. The method of claim 42, wherein the cosmetic, pharmaceutical or other topical agent is selected from the group consisting of clotrimazole, ketoconazole, miconazole, griseofulvin, econazole, metronidazole, hydroxyzine, diphenhydramine, pramoxine, lidocaine, procaine, mepivacaine, monobenzone, erythromycin, tetracycline, clindamycin, meclocycline, hydroquinone, hydroquinone monoether, minocycline, naproxen, ibuprofen, theophylline, cromolyn, albuterol, retinol, retinyl acetate, retinyl palmitate, retinoic acid, 13-cis retinoic acid, hydrocortisone, hydrocortisone 21-acetate, hydrocortisone 17-valerate, hydrocortisone 17-butyrate, betamethasone valerate, betamethasone dipropionate, triamcinolone acetonide, fluocinonide, clobetasol propionate, benzoyl peroxide, crotamiton, propranolol, promethazine, salicylic acid, vitamin E and vitamin E acetate.*

* * * * *